(12) United States Patent
Vatner et al.

(10) Patent No.: US 8,871,735 B2
(45) Date of Patent: Oct. 28, 2014

(54) METHODS AND COMPOSITIONS FOR PROVIDING CARDIAC PROTECTION

(71) Applicant: University of Medicine and Dentistry of New Jersey, Somerset, NJ (US)

(72) Inventors: Stephen F. Vatner, New York, NY (US); Dorothy E. Vatner, New York, NY (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/668,897

(22) Filed: Nov. 5, 2012

(65) Prior Publication Data

US 2013/0131005 A1    May 23, 2013

Related U.S. Application Data

(63) Continuation-in-part of application No. 12/735,679, filed as application No. PCT/US2009/000836 on Feb. 9, 2009.

(60) Provisional application No. 61/063,981, filed on Feb. 7, 2008.

(51) Int. Cl.
    *A01N 43/04*     (2006.01)
    *A61K 31/70*     (2006.01)
    *A61K 31/7076*   (2006.01)

(52) U.S. Cl.
    CPC .................. *A61K 31/7076* (2013.01)
    USPC .................... 514/46; 514/42; 514/43; 514/45

(58) Field of Classification Search
    None
    See application file for complete search history.

(56) References Cited

PUBLICATIONS

Jugdutt et al. Molecular and Cellular Biochemistry (2005), vol. 270, pp. 177-200.*
Baines et al. Journal of Molecular and Cellular Cardiology (2005), vol. 38, pp. 47-62.*
Zhao et al. Cardiovascular Research (2003), vol. 59, pp. 132-142.*
Ishikawa et al. "Genetic Manipulation and Function Analysis of cAMP Signalling in Cardiac Muscle: Implications for a New Target of Pharmacotherapy" Biochemical Society Transactions 2005 33(6):1337-1340.
Iwatsubo, K. and Ishikawa, Y. "Therapeutic Targets for Heart Failure: Beyond Beta-Adrenergic and Renin-Angiotensin System Blockade" Recent Patents on Cardiovascular Drug Discovery 2008 3:37-44.
Iwatsubo et al. "Direct Inhibition of Type 5 Adenylyl Cyclase Prevents Myocardial Apoptosis without Functional Deterioration" Journal of Biological Chemistry 2004 279(39):40938-40945.
Levy et al. "Metal Coordination-Based Inhibitors of Adenylyl Cyclase: Novel Potent P-site Antagonists" Journal of Medicinal Chemistry 2003 46:2177-2186.
Okumura et al. "Disruption of Type 5 Adenylyl Cyclase Preserves Cardiac Function Against Chronic Catecholamine Stress" Journal of Cardial Failure 2007 13(6):S46.
Rottlaender et al. "Functional Adenylyl Cyclase Inhibition in Murine Cardiomyocytes by 2'(3')-0-(N-Methylanthraniloyl)-Guanosine 5'-(gamma-Thio)triphosphate" The Journal of Pharmacology and Experimental Therapeutics 2007 321(2):608-615.
Vasquez et al. "Optimal Dosing of Dobutamine for Treating Post-Resuscitation Left Ventricular Dysfunction" Resuscitation 2004 61(2):199-207.
Office Communication dated Sep. 25, 2012 from U.S. Appl. No. 12/735,679, filed Oct. 1, 2010.
International Search Report from PCT/US2009/000836, May 13, 2009.
International Preliminary Report on Patentability from PCT/US2009/000836, Aug. 10, 2010.

* cited by examiner

*Primary Examiner* — Patrick Lewis
(74) *Attorney, Agent, or Firm* — Licata & Tyrrell P.C.

(57) ABSTRACT

The invention provides a method of reducing infarct size and/or limiting, decreasing and/or inhibiting reperfusion injury and/or ameliorating heart failure in a patient comprising administering a pharmaceutically effective amount of at least one compound capable of inhibiting AC5 to the patient. The compound capable of inhibiting AC5 is particularly effective when administered during or after reperfusion in patients suffering from an ischemic injury.

10 Claims, 19 Drawing Sheets

ARA-ADE

ADENOSINE

*p<0.05 vs. PRE AraAde

METHODS AND COMPOSITIONS FOR PROVIDING CARDIAC PROTECTION

This patent application is a continuation-in-part of U.S. application Ser. No. 12/735,679, filed Oct. 1, 2010, which is the U.S. National Stage of PCT/US2009/000836, filed Feb. 9, 2009, which claims the benefit of priority from U.S. Provisional Patent Application No. 61/063,981, filed Feb. 7, 2008, teachings of each of which are herein incorporated by reference in their entirety.

FIELD OF THE INVENTION

The invention relates to the use of Type 5 Adenylyl Cyclase (hereinafter "Type 5 AC" or "AC5") inhibitors to treat and prevent cardiac diseases or ailments. In particular, the invention relates to use of AC5 inhibitors to reduce infarct size, limit reperfusion injury and/or ameliorate heart failure progression when administered to a patient following an ischemic injury at the time of reperfusion or after reperfusion.

BACKGROUND OF THE INVENTION

Cardiovascular disease is a critical health issue in Western countries. The leading cause of death is heart failure (HF), which represents not only a significant problem to be addressed but also involves a large amount of health care costs. According to the American Heart Association, over 5.5 million patients were diagnosed with congestive HF in the U.S. The estimated annual direct and indirect healthcare costs associated with chronic HF in the U.S. alone exceeds $24 billion. The projection of morbidity and mortality will be continuously increased in the next 15 years because of the significant increase in population. Therefore, improvement of HF therapy is extremely important.

β-blockers are now widely used for treating HF; however, despite the well established effect in clinical trials, some patients are intolerant to β-blocker therapy because they occasionally exacerbate HF by attenuation of cardiac contraction (Bristow M R. Circulation. 2000; 101(5):558-569; Hunt et al. Journal of the American College of Cardiology. 2005; 46(6):e1-e82; Ko et al. Arch Intern Med. 2004; 164 (13):1389-1394.). Therefore, a new approach to β-blocker therapy is indicated and could save such patients.

HF is the common endpoint of many different forms of heart disease, and a pathophysiologic state with impaired cardiac function such that the heart cannot provide a sufficient output for organs and tissues. Despite that, developments in medical treatments have resulted in reducing the overall mortality rate from heart disease over the last several decades; however, death from chronic HF still continues to increase. With chronic HF, sympathetic activity is known to be increased to compensate for impaired cardiac function. Such increase of sympathetic activity stimulates cardiac contractility, thus, HF is improved. However, paradoxically, elevated sympathetic activity also causes myocardial apoptosis. Myocardial apoptosis results in a loss of cardiac myocytes, thus, contractile function is impaired. Increased oxidative stress is also a major causal factor for the progression of HF (Giordano et al. J Clin Invest. March 2005; 115(3):500-508.).

AC is a 12-transmembrane protein that catalyzes the conversion of ATP to cAMP upon the stimulation of various G-protein coupled receptors such as β-adrenergic receptor (β-AR). Nine mammalian AC subtypes have been identified, and each subtype shows distinct tissue distributions, and biological and pharmacological properties (Iwatsubo et al., Endocr Metab Immune Disord Drug Targets. September 2006; 6(3):239-247). Stimulation of G protein-coupled receptors induces binding of the stimulatory Gα subunit (Gsα) to AC, and enhances its catalytic activity to convert ATP into cAMP. cAMP regulates multiple downstream molecules, via protein kinase A (PKA) and exchange protein activated by cAMP (Epac).

A series of studies in genetically-engineered mice has demonstrated the crucial role of AC5, a major cardiac subtype of AC, in progression of heart failure (HF). Disruption of AC5 protects against the development of several type of HF (Okumura et al., Circulation. Oct. 16, 2007; 116(16):1776-1783; Okumura et al., PNAS. Aug. 19, 2003; 100(17):9986-9990; Yan et al., Cell. Jul. 27, 2007; 130(2):247-258). Interestingly, prevention of aging-related HF resulted in prolonged lifespan; therefore, the development of a chemical inhibitor of AC5 would be extremely valuable.

AC5 is a major cardiac subtype of AC, which provides 20% of total AC activity in the heart, and recent studies including ours revealed its crucial role in progression of HF (Iwatsubo et al., J Biol. Chem. Sep. 24, 2004; 279(39):40938-40945; Okumura et al., Circ Res. Aug. 22, 2003; 93(4):364-371). AC5KO mice showed decreased myocardial apoptosis and preserved cardiac function in HF models induced by chronic pressure overload (Okumura et al. Proceedings of the National Academy of Sciences. 2003; 100(17):9986-9990), chronic β-AR stimulation (Okumura et al., Circulation. 2007; 116(16):1776-1783) and aging (Yan et al., Cell. Jul. 27, 2007; 130(2):247-258). In all these HF models, myocardial apoptosis, which is a major cause for progression of HF, was significantly decreased in AC5KO, indicating that AC5 plays a central role in inducing apoptosis and subsequent development of HF. Moreover, AC5Tg showed decreased left ventricular ejection fraction (LVEF) and increased apoptosis in response to chronic pressure overload, indicating that AC5 accelerates the progression of HF by inducing myocardial apoptosis. These data strongly suggest that among mechanisms by which myocardial apoptosis occurs such as renin-angiotensin-aldosterone, death receptor and calcium signaling, sympathetic activity overdrive, particularly via stimulating AC5, plays a major role in inducing myocardial apoptosis and development of HF.

Classic inhibitors of AC, known as P-site inhibitors, have been studied since the 1970's. It was first thought that there was an adenosine-reactive site within intracellular domain of AC, the "P" site, which inhibits the catalytic activity of AC. In spite of their similar chemical structure to the substrate ATP, P-site inhibitors showed un- or non-competitive inhibition with respect to ATP, indicating little influence on molecules which have ATP-binding site (Londos et al., Proc Natl Acad Sci USA. December 1977; 74(12):5482-5486). Although it has been a very attractive idea to develop P-site inhibitors with enhanced AC subtype selectivity, few attempts have been successful due to the difficulties of experiments in which the selectivity of each AC isoforms can be examined in vitro. However, several groups including ours have developed such experimental systems using the baculovirus-based recombinant AC overexpression system (Iwatsubo et al., J Biol. Chem. Sep. 24, 2004; 279(39):40938-40945; Onda et al. J Biol. Chem. Dec. 21, 2001; 276(51):47785-47793).

9-β-D-arabinofuranosyladenine (Ara-Ade) contains an adenosine-like structure where the adenine ring is essential not only for binding to the AC catalytic core but also for penetrating the plasma membrane (Iwatsubo et al. J Biol. Chem. 2004; 279(39):40938-40945, Onda et al. J Biol. Chem. 2001; 276(51):47785-47793. Tesmer et al. Biochemistry. 2000; 39(47):14464-14471. Tesmer et al. Science. 1999; 285(5428):756-760). For example, NKY80, which does not contain adenosine within its structure, showed moderate inhibition of purified AC5 protein in vitro, but it did not inhibit cAMP accumulation in cultured cardiac myocytes, indicating that the adenosine structure seems essential for penetrating the plasma membrane (Iwatsubo, et al. J Biol. Chem. 279(39):40938-40945). In addition, adenosine hardly crosses through the blood-brain barrier (BBB) (Isakovic et al. Journal of Neurochemistry. 90(2):272-286.), having little influence on brain function; this is important because AC5 is also expressed in the striatum other than the heart, thus by passing BBB AC5 inhibitors may cause adverse effects in the brain.

SUMMARY OF THE INVENTION

The invention provides compositions and methods for treating cardiac diseases by administering to a patient an effective amount an AC5 inhibitor.

In a first aspect, the invention provides a method of treating a cardiac disease comprising administering a pharmaceutically effective amount of at least one compound capable of inhibiting AC5 to a patient. The compound capable of inhibiting AC5 may be administered singly or in combination with another agent, such as, for instance a β-blocker. In some embodiments, the AC5 inhibiting compound is 9-β-D-arabinofuranosyladenine (Ara-Ade). The compounds may be administered in an amount of about 1 to about 200 mg/kg/day, about 1 to about 100 mg/kg/day, about 10 to about 80 mg/kg/day, about 12 to about 40 mg/kg/day or about 15 to about 25 mg/kg/day. In some embodiments, the compound is administered parenterally. The cardiac disease may be, for instance, myocardial infarction (MI) or heart failure (HF).

The compound capable of inhibiting AC5 may be administered alone or in conjunction with one or more other active agents. In a second aspect, the invention provides a method of treating a heart attack comprising administering a pharmaceutically effective amount of at least one compound capable of inhibiting AC5 to a patient. Also, this second aspect features methods of improving the chances of survival after a heart attack. The compound capable of inhibiting AC5 may be administered singly or in combination with another agent, such as, for instance a β-blocker. In some embodiments, the AC5 inhibiting compound is 9-β-D-arabinofuranosyladenine (Ara-Ade). The compounds may be administered in an amount of about 1 to about 100 mg/kg/day, about 10 to about 40 mg/kg/day or about 15 to about 25 mg/kg/day. In some embodiments, the compound is administered parenterally.

In a third aspect, the invention provides a method of inhibiting myocardial apoptosis comprising administering a pharmaceutically effective amount of at least one compound capable of inhibiting AC5 to a patient. The compound capable of inhibiting AC5 may be administered singly or in combination with another agent, such as, for instance a β-blocker. In some embodiments, the AC5 inhibiting compound is 9-β-D-arabinofuranosyladenine (Ara-Ade). The compounds may be administered in an amount of about 1 to about 100 mg/kg/day, about 10 to about 40 mg/kg/day or about 15 to about 25 mg/kg/day. In some embodiments, the compound is administered parenterally.

In a fourth aspect, the invention provides a method of treating heart failure comprising administering a pharmaceutically effective amount of at least one compound capable of inhibiting AC5 to a patient. The heart failure may, for instance, occur after a heart attack or myocardial infarction. The compound capable of inhibiting AC5 may be administered singly or in combination with another agent, such as, for instance a β-blocker. In some embodiments, the AC5 inhibiting compound is 9-β-D-arabinofuranosyladenine (Ara-Ade). The compounds may be administered in an amount of about 1 to about 100 mg/kg/day, about 10 to about 40 mg/kg/day or about 15 to about 25 mg/kg/day. In some embodiments, the compound is administered parenterally.

In a fifth aspect, the invention provides a method of reducing infarct size and/or limiting, decreasing and/or inhibiting reperfusion injury and/or ameliorating or inhibiting heart failure progression comprising administering a pharmaceutically effective amount of at least one compound capable of inhibiting AC5 to a patient. The reduction in infarct size and/or limitation in reperfusion injury may, for instance, occur after an ischemic injury. Administration of the AC5 inhibitor during or after reperfusion following ischemic injury is particularly effective in reducing infarct size and/or limiting, decreasing and/or inhibiting reperfusion injury. For this embodiment, the AC5 inhibitor may resemble adenosine structurally. The AC5 inhibitor may be administered singly or in combination with another agent, such as, for instance a β-blocker. In some embodiments, the AC5 inhibiting compound is 9-β-D-arabinofuranosyladenine (Ara-Ade). In this embodiment, the compound may be administered in an amount far lower, for example less that 1 mg/kg, less than 0.1 mg/kg, or about 0.06 mg/kg, than the antiviral doses of 10-30 mg/kg used in humans. In this embodiment, the compound can be administered as a single i.v. infusion.

DETAILED DESCRIPTION OF THE PREFERRED EMBODIMENTS

Definitions

Figure 1:
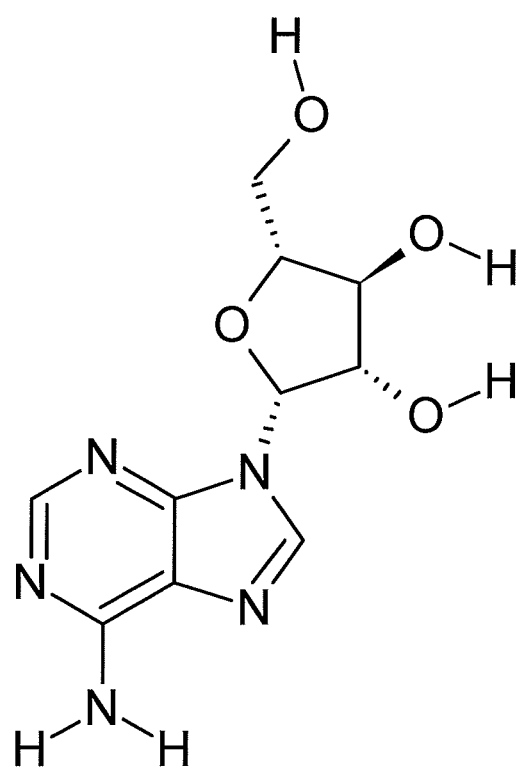
FIG. 1 provides the chemical structure of Ara-Ade compared to the structurally similar compound of adenosine.
Figure 1:
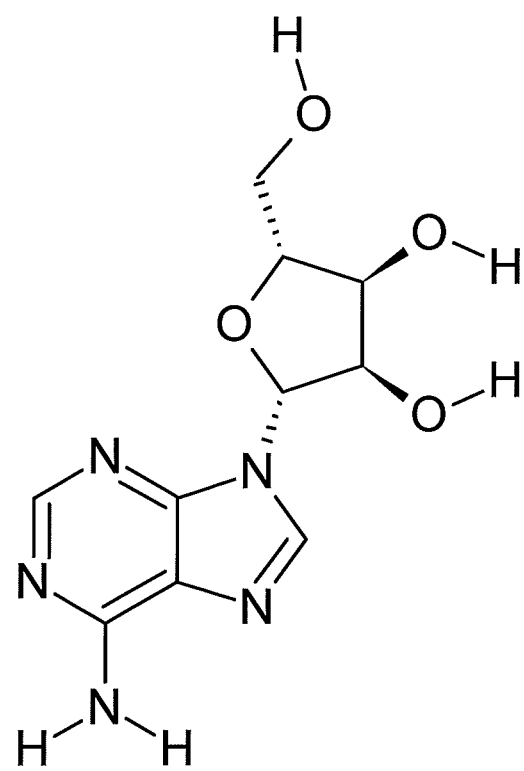

By "heart failure" (HF) is meant inability of the heart to maintain the circulation of blood sufficient to sustain life.

By "heart attack" is meant myocardial infarction (MI).

"Inhibitor of AC5" includes but is not limited to, any suitable molecule, compound, protein or fragment thereof, nucleic acid, formulation or substance that can regulate AC5 activity in such a way that AC5 activity is decreased. The inhibitor can include, but is not limited to, the specifically identified ribose-substituted P-site ligands such THFA 9-(tetrahydro-2-furyl)adenine and CPA 9-(cyclopentyl)adenine or 2-amino-7-(2-furanyl)-7,8-dihydro-5(6H)-quinazoline (NKY80) and 9-β-9-β-arabinofuranosyladenine (Ara-Ade).

"Left Ventricular Ejection Fraction (LVEF)" is an indicator of left ventricular systolic function and is calculated either by echocardiograph or radionuclide ventriculography. LVEF is the fraction of blood ejected in systole and is calculated as (LV Volume at end of diastole-LV Volume at end of systole)/(LV Volume of blood at end of diastole).

"Mammal" refers to any animal classified as a mammal, including humans, domestic and farm animals, and zoo, sports, and pet companion animals, and other domesticated animal such as, but not limited to, cattle, sheep, ferrets, swine, horses, poultry, rabbits, goats, dogs, cats, and the like.

"Patient" refers to a mammal, preferably a human, in need of treatment for a condition, disorder or disease.

Pharmaceutically acceptable salts include salts of compounds derived from the combination of a compound and an organic or inorganic acid. These compounds are useful in both free base and salt form. In practice, the use of the salt form amounts to use of the base form; both acid and base addition salts are within the scope of the present invention.

Pharmaceutically acceptable acid addition salt refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

Pharmaceutically acceptable base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation.

"Therapeutically effective dose" refers to the dose that produces the effects for which it is administered.

"Treat" and "treatment" refers to both therapeutic treatment and prophylactic or preventative measures, wherein the object is to prevent or slow down (lessen) an undesired physiological condition, disorder or disease or to obtain beneficial or desired clinical results. For purposes of this invention, beneficial or desired clinical results include, but are not limited to, alleviation of symptoms; diminishment of extent of condition, disorder or disease; stabilization (i.e. not worsening) a state or condition, disorder or disease; delay or slowing of a condition, disorder, or disease progression; amelioration of the condition, disorder or disease state; remission (whether partial or total), whether detectable or undetectable; or enhancement or improvement of a condition, disorder or disease. Treatment includes eliciting a cellular response that is clinically significant, without excessive side effects. Treatment also includes prolonging survival as compared to expected survival without treatment Classic inhibitors of AC include adenosine analogs or P-site inhibitors, and MDL12330A, a non-nucleic acid inhibitor. However, not much was known about the isoform selectivity of these inhibitors. Classic P-site inhibitors with phosphate at the 3' position such as 2'-d-3'-AMP and 3'-AMP potently inhibited AC catalytic activity. 2'-d-3'-AMP potently inhibited AC5 and AC3 while to a lesser degree AC2; the selectivity ratio was 27 between AC5 and AC2. The $IC_{50}$ values for each isoform were calculated to be 0.82 micro M for AC5, 2.8 micro M for AC3 and 22.4 micro M for AC2. In contrast, ribose-substituted P-site inhibitors, such as THFA and CPA, potently inhibited AC5 while they inhibited AC2 and AC3 only to a modest degree in the presence of Gs-α/GTPαS/forskolin. The $IC_{50}$ value was calculated as 2.2 µM for AC5, 101 µM for AC3 and 285 µM for AC2. It was previously noted that AC2 was less sensitive to THFA than the other isoforms, giving a selectivity ratio of 1.8 when compared between AC6 and AC2. Inventors found that the selectivity ratio was even greater (130) between AC5 and AC2.

The present invention demonstrates that 9-β-arabinofuranosyladenine (Ara-Ade), now used for treating viral infections, shows potent and selective AC5 inhibition (Physicians' Desk Reference 2006. Montvale, N.J.: Thomson P D R; 2006; Kleymann G. Expert Opin Investig Drugs. 2003; 12(2):165-183; Whitley Ann Pharmacother. 1996; 30(9):967-971; Whitley et al., Antimicrob Agents Chemother. November 1980; 18(5):709-715). In addition, Ara-Ade increases the survival rate in the post-myocardial infarction (post-MI) period, indicating that Ara-Ade has salutary effect in post-MI HF. Finally, AC5KO exhibits activation of mitogen-activated protein/extracellular signal-regulated kinase (MEK)1-extracellular regulated kinases (ERK)1/2 signaling pathway in the heart, which is a major signaling in cardiac protection (Bueno et al., Circ Res. 2002; 91(9):776-781; Lips et al., In Vivo. Circulation 2004; 109(16):1938-1941; Bueno et al., Embo J. 2000; 19(23):6341-6350).

Amantadine, which was originally developed as a drug for treating Parkinson's disease, but is now widely used for treating virus infection such as influenza or hepatitis C virus (Jefferson et al., Cochrane Database Syst Rev. 2006(2): CD001169; Wohnsland et al., Clin. Microbiol. Rev. 2007; 20(1):23-38).

TABLE 1

$IC_{50}$ and selectivity ratios of AC inhibitors in recombinant AC proteins. 2'5'-dd-Ado and Ara-Ade are potent, selective AC5 inhibitors. Selectivity ratio for AC5 is the ratio of $IC_{50}$ for AC5 to that for AC2 or AC3, which indicates the selectivity for AC5 among other subtypes.

|  |  | 2'5'-dd-Ado | Ara-Ade | PMC-6 |
|---|---|---|---|---|
| $IC_{50}$ | AC2 | 2382 | 7202 | 65.3 |
|  | AC3 | 253 | 375 | 11.1 |
|  | AC5 | 1.6 | 9.8 | 0.32 |
| Selectivity | AC5/AC2 | 0.00067 | 0.0014 | 0.0049 |
| ratio for AC5 | AC5/AC3 | 0.0063 | 0.027 | 0.029 |

Ara-Ade is an Alternative to (β-AR blockers (β-Blockers):

β-blockers are well-established drugs for treating HF (Lancet. 1999; 353(9169):2001-2007). Several large trials have demonstrated that the long-term administration of β-blockers to patients after myocardial infarction improves survival, and thus β-blockers are now used as a first-line drug for post-MI HF (lama. 1981; 246(18):2073-2074; Hjalmarson et al., Lancet. 1981; 2(8251):823-827; Mosca et al., Circulation 2004; 109(5):672-693). However, β-blockers occasionally exacerbate HF due to contractile dysfunction. Therefore, some patients are intolerant to the administration of β-blockers, and the number of such patients who cannot benefit from β-blockers is, roughly estimated, over 1.3 million (Ko et al., Arch Intern Med. 2004; 164(13):1389-1394; Hunt, Journal of the American College of Cardiology. 2005; 46(6):e1-e82; Bristow, Circulation 2000; 101(5):558-569; Mannino et al., MMWR Surveill Summ. 2002; 51(1):1-13; Sidney et al., Chest 2005; 128(4):2068-2075). Thus, an agent that could exert similar actions to β-blockers, but does not affect contractile function, would save a considerable number of patients. Both AC5KO and AC5Tg showed similar left ventricular (LV) function to wild type (WT), indicating the minor role of AC5 in contractile function (Okumura et al., PNAS 2003; 100(17):9986-9990). Also, chronic infusion of Ara-Ade did not affect basal LV function (see preliminary studies) indicating that Ara-Ade exerts its effect without severely deteriorating LV function and might be a safer alternative to β-blockers.

Also, β-blockers are not recommended to HF patients with diabetes mellitus or chronic obstructive pulmonary disease (COPD) due to adverse effect raised from wide distribution of β-adrenergic receptors (β-AR). These considerable number of "β blocker-intolerant" HF patients may be rescued by Ara-Ade. Since AC5 is mainly expressed in the heart and the brain, Ara-Ade would have less adverse effects than β blocker in patients with diabetes mellitus or COPD. Indeed, there has been no report of sever adverse effects of Ara-Ade in diabetes or COPD. The attempt develop such "enzymatic cAMP regulation in a organ-specific manner" has already produced successful outcome, e.g. milrinone as a phosphodiesterase (PDE)3 inhibitor for the treatment of heart failure, or sildenafil citrate as a PDE 5 inhibitor for erectile dysfunction (Degerman et al., J Biol. Chem. Mar. 14, 1997; 272(11):6823-6826; Corbin et al., J Biol. Chem. 1999; 274(20):13729-13732). Putting together, Ara-Ade would be a drug for treating heart failure with less adverse effects than β-blockers. MEK1-ERK1/2 Pathway Plays a Major Role in Protection of Cardiomyocytes.

Emerging evidence demonstrates that ERK activation plays a central role in protecting cardiomyocytes from apoptosis. Transgenic mice expressing an activated MEK1 mutant in the heart, which show singular ERK1/2 activation, were resistant to ischemia-reperfusion-induced apoptosis. More recently, erk1$^{-/-}$ and erk2$^{+/-}$ gene-targeted mice showed a significant increase in myocardial injury and cellular apoptosis following ischemia-reperfusion injury. In addition, recent studies have suggested the downstream molecules of ERK in protection of cardiomyocytes, such as cyclooxygenase-2 (Cox-2), atrial natriuretic factor (ANF) expression, PKCε and p90 ribosomal S6 kinases (RSK), indicating that ERK plays a central role in inhibiting myocardial apoptosis. A very recent study in AC5KO demonstrated that old AC5KO are protected from myocardial apoptosis and aging-related LV dysfunction, and which is largely mediated by the MEK1/-ERK1/2 signaling pathway. In addition, AC5KO mice showed that, as a result of protection against aging-related HF, increased lifespan of 30%, indicating that MEK1-ERK1/2 activation induced by AC5 deletion leads not only protection against HF but also prolonged lifespan. Since PKA is known to inhibit the MEK1/ERK1/2 pathway through inactivating Raf-1, an upstream molecule of MEK1, these data indicate that deletion of AC5 activates MEK1-ERK1/2 pathway through decreasing PKA activity. Accordingly, it is important to examine the effect of Ara-Ade on MEK1-ERK1/2 activation in post-MI hearts (Lips et al., Circulation 2004; 109(16):1938-1941; Bueno et al., Embo J. 2000; 19(23):6341-6350; Baines et al., Journal of Molecular and Cellular Cardiology. 2005; 38(1): 47-62; Adderley et al., J. Biol. Chem. 1999; 274(8):5038-5046; Jankowski et al., Proceedings of the National Academy of Sciences 2001; 98(20):11765-11770; Baines et al., Circ Res. 2002; 90(4):390-397; Smith et al., J. Biol. Chem. 1999; 274(5):2893-2898; Burgering et al., Trends Biochem Sci. 1995; 20(1):18-22).

A series of studies in genetically engineered mice demonstrated the major role of AC5 in progression of HF. We examined chronic β-AR stimulation with isoproterenol (ISO) infusion in WT and AC5KO (Okumura et al., Circulation 2007; 116(16):1776-1783). Chronic ISO infusion increased myocardial apoptosis in both WT and AC5KO, however, the degree of increase was significantly lower in AC5KO mice than in WT (FIG. 2a), suggesting that the deletion of AC5 prevented ISO-induced apoptosis. In addition, LVEF was decreased by chronic ISO in both WT and AC5KO mice, but the magnitude of decrease was significantly greater in WT than in AC5KO mice (FIG. 2b), indicating that deletion of AC5 inhibited the progression of HF through inhibiting myocardial apoptosis. Moreover, we examined the effect of chronic ISO infusion in AC5Tg, and AC5Tg showed decreased LVEF (FIG. 2c), demonstrating that AC5 plays a central role in developing HF.

In addition to the chronic ISO infusion HF model, since AC5KO mice also exhibited preserved LV function in chronic pressure overload, we examined the effect of chronic pressure overload in AC5Tg. AC5Tg significantly decreased LVEF after 1 week of transaortic constriction (FIG. 2d), indicating that AC5 overexpression develops more severe LV decompensation. These results suggested that deletion of AC5 is beneficial for different models of HF, and that it is feasible that pharmacological inhibition of AC5 prevents myocardial apoptosis and the progression of HF.

Figure 3:
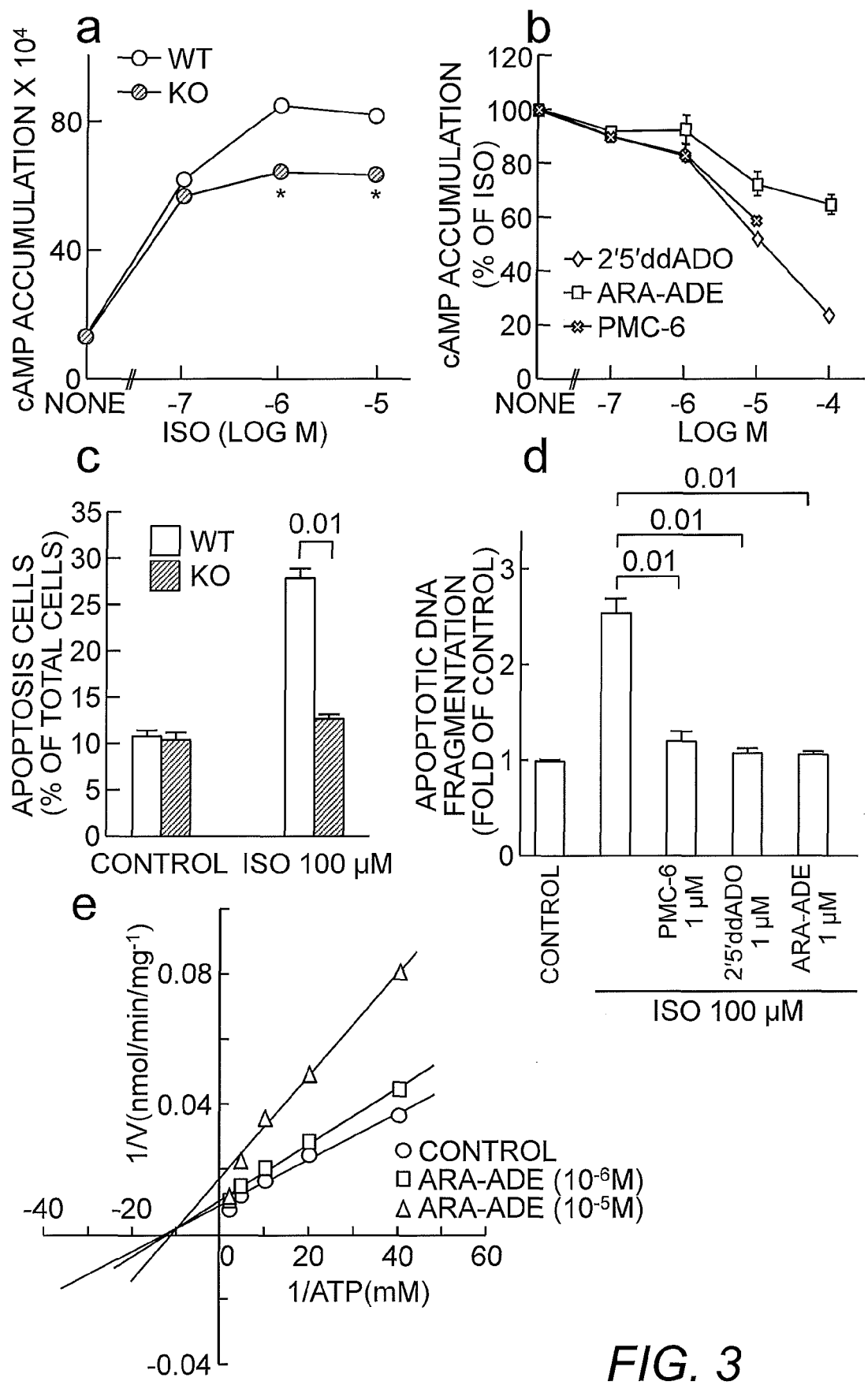
FIG. 3(a-d) shows that AC5 inhibitors (1R, 4R-3-(6-amino-purin-9-yl)-cyclopentanecarboxylic acid hydroxyamide (PMC-6), 2',5'-Dideoxyadenosine (2'5' ddAdo(2'5' ddAdo) and Ara-Ade) prevent myocardial apoptosis. a) cAMP accumulation in mouse cardiac myocytes from AC5KO and WT was measured with increasing ISO concentrations. Decrease in cAMP in AC5KO was observed only at high ISO concentrations. *, $p<0.01$ versus WT. n=5. b) cAMP accumulation in mouse cardiac myocytes was measured with 10 μM ISO in the presence or absence of AC5 inhibitors. c) Cultured cardiac myocytes from AC5KO showed protection against ISO-induced apoptosis. n=5. d) Apoptosis was evaluated by DNA fragmentation ELISA. Cultured cardiac myocytes were incubated with 100 μM ISO in the presence or absence of AC5 inhibitors at the indicated concentrations for 48 h. All AC5 inhibitors prevented myocardial apoptosis. n=5. (e) Double reciprocal plot showed that Ara-Ade exhibits un-competitive or non-competitive inhibition with respect to ATP.

AC5 inhibitors including Ara-Ade prevent apoptosis in cultured cardiac myocytes. As shown in FIG. 3a, since AC5 provides 20% of total AC activity in cardiac myocytes, and the concentrations at which AC5 inhibitors decrease total AC activity by 20% (FIG. 3b) were used in an apoptosis assay. As shown in FIG. 3d, AC5 inhibitors including Ara-Ade completely abolished ISO-induced apoptosis, indicating that AC5, among other subtypes of AC, play the most major role in inducing apoptosis in cardiac myocytes. This was supported by the data that cultured cardiac myocytes from AC5KO protected against ISO-induced apoptosis (FIG. 3c). On the other hand, since Ara-Ade has a similar structure to ATP, we examined double-reciprocal plots of the rate of type 5 AC catalytic activity against the substrate ATP. Ara-Ade showed un-competitive or non-competitive with respect to ATP, suggesting that Ara-Ade has little effects on molecules with ATP binding sites.

Figure 2:
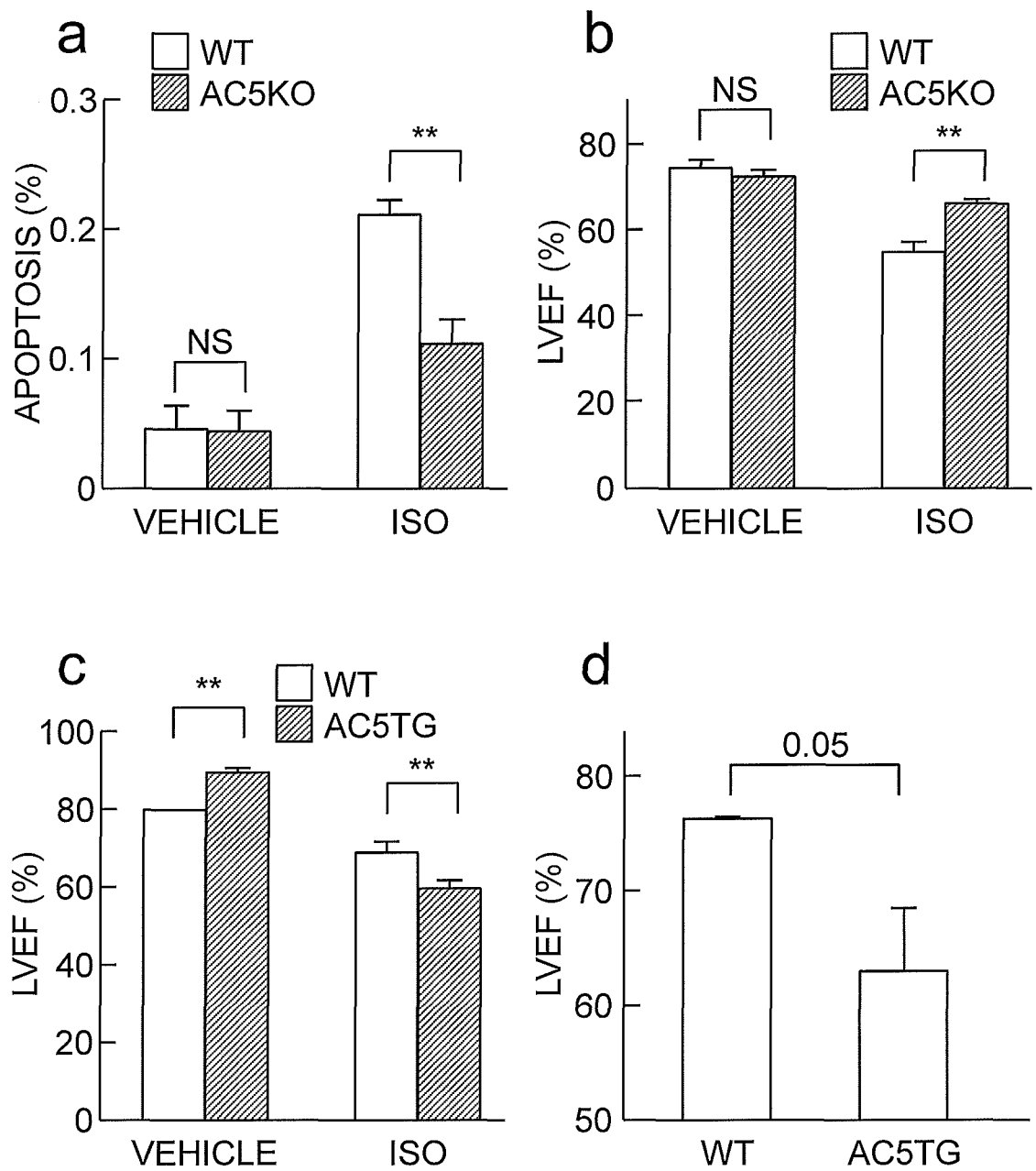
FIG. 2 demonstrates that AC5 play a major role in developing HF induced by 1 week chronic ISO (isoproterenol) infusion (a, b and c) and 3 week chronic pressure overload (d) in mice. a) Apoptosis in the left ventricle (LV) was evaluated by TUNEL assay. TUNEL-positive myocytes in LV myocardium were counted. , $p<0.01$, n=7-10 each. b) Echocardiographic measurements of LV function were performed in wild type (WT) and AC5 knock out (AC5KO) mice after chronic isoproterenol (ISO) infusion. LVEF was decreased in both WT and AC5KO mice after chronic ISO, but the magnitude of the decrease was greater in WT than in AC5KO mice. $p<0.01$, n=4-5. c) LVEF in AC5Tg was examined. LVEF was lower in AC5Tg after chronic ISO infusion whereas LVEF was higher in vehicle, indicating AC5Tg develops more severe LV dysfunction in response to chronic ISO infusion. n=6-7. **, $p<0.01$. d) AC5Tg showed decreased LVEF in response to chronic pressure overload. n=5.
Figure 4:
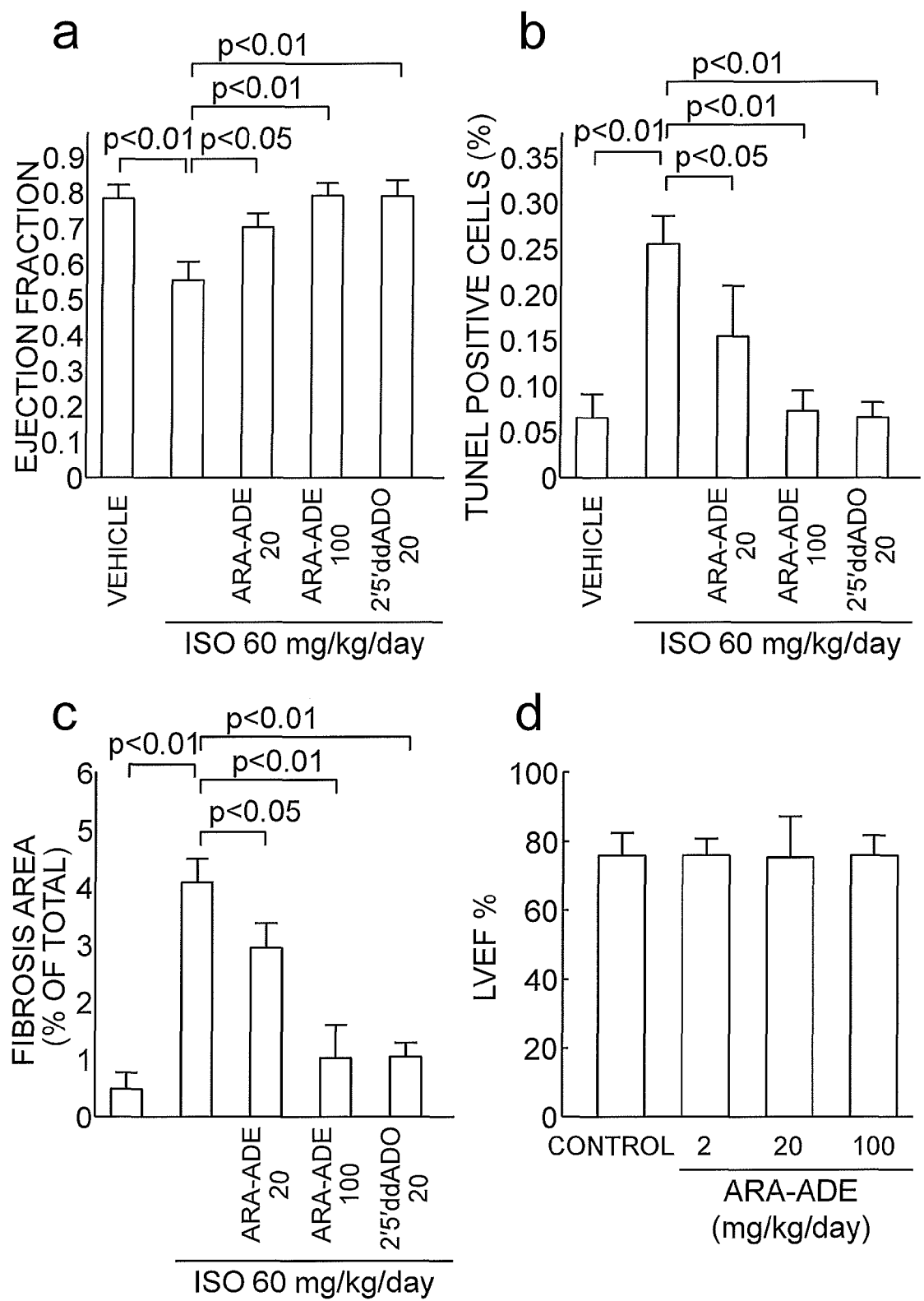
FIG. 4 demonstrates that AC5 inhibitors prevent LV dysfunction, apoptosis and cardiac fibrosis in chronic ISO infusion. ISO with or without AC5 inhibitors were chronically infused with osmotic mini-pump implanted subcutaneously at indicated doses for 1 week in c57Bl/6 mice. Mice were then subjected to echocardiography (a) and the hearts were removed and subjected to pathological examinations such as myocardial apoptosis (b) and fibrosis (c). n=4-8. (d) Chronic infusion of Ara-Ade alone for 1 week did not change LVEF in mice. n=5.

In addition to cultured cardiac myocytes, we examined the effects of the AC5 inhibitors, Ara-Ade and 2'5' ddAdo, in the chronic ISO infusion model. Both Ara-Ade and 2'5' ddAdo inhibited the ISO-induced decrease in LVEF (FIG. 4a), myocardial apoptosis (FIG. 4b) and cardiac fibrosis (FIG. 4c), and these results are consistent with the study in AC5KO mice (FIG. 2). On the other hand, Chronic Ara-Ade infusion did not affect basal LVEF (FIG. 4d), this is also consistent with the date in AC5KO such that basal LVEF is similar between AC5KO and WT. This indicated that Ara-Ade administrations at these concentrations are not likely to cause HF exacerbation which is occasionally observed in β-blockers. It is notable that the concentration of Ara-Ade we have used (20 mg/kg/day) is similar to that which is clinically used to treat virus infection (15 mg/kg/day). Also, in intravenous infusion of Ara-Ade (10 mg/kg) in human, the plasma Cmax is 4.8 µM, which is similar to the effective concentration in inhibiting apoptosis (10 µM, FIG. 3d). Together, these Ara-Ade's data strongly suggest the feasibility of application of Ara-Ade to an AC5 inhibitor for treating HF.

Figure 5:
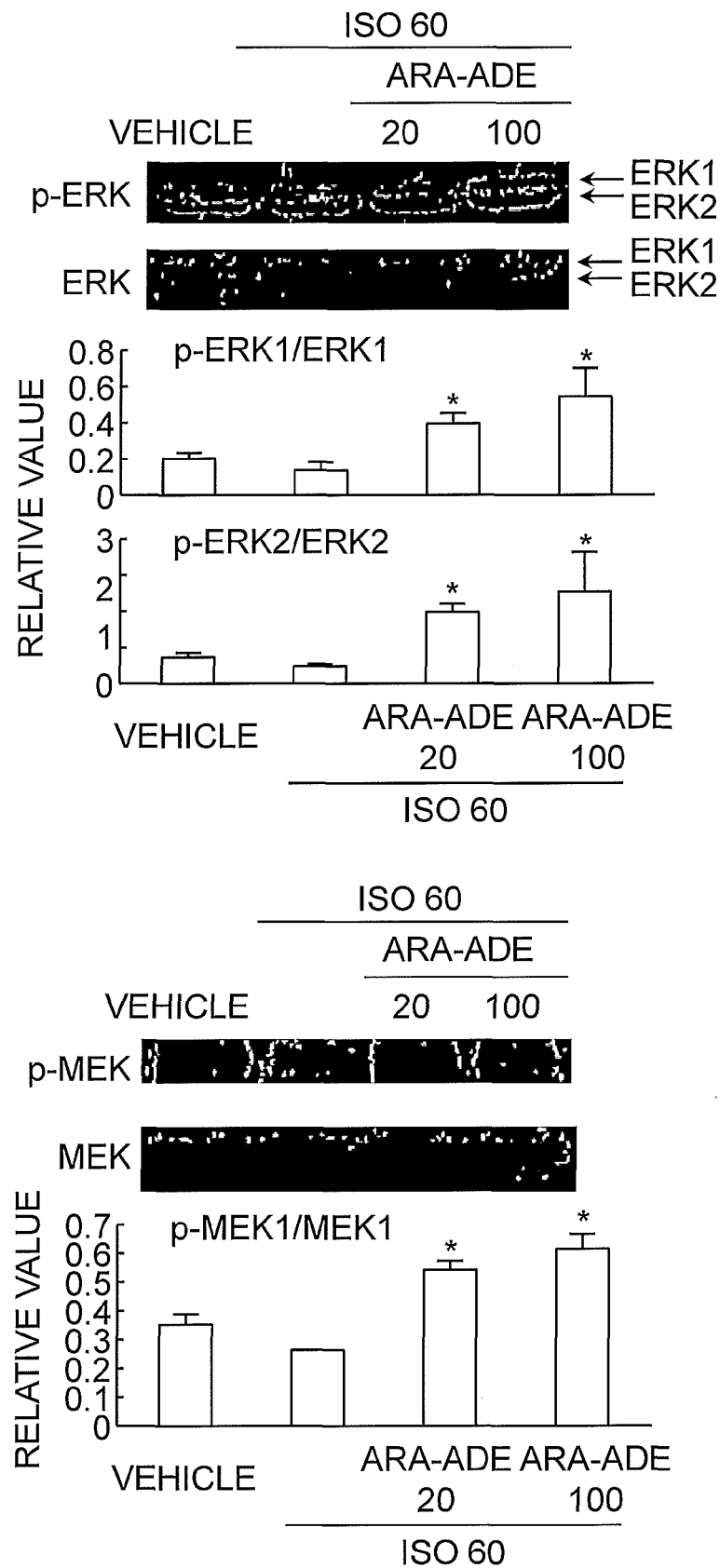
FIG. 5 demonstrates that Ara-Ade activates ERK signaling, which is known as anti-apoptotic signaling pathway in cardiac myocytes. The activities of MEK1 and ERK1/2 signaling pathway were examined by measuring the phosphorylated and total forms. After chronic ISO infusion for 1 week (60 mg/kg/day; ISO60) with or without chronic infusion of Ara-Ade (20 mg/kg/day; Ara-Ade 20, or 100 mg/kg/day; Ara-Ade 100), the hearts were removed and subjected to western blot analysis. pERK and pMEK were increased by Ara-Ade, suggesting that Ara-Ade protects against cardiac myocyte apoptosis via the MEK/ERK signaling pathway *, p<0.01 versus ISO60. n=4.

Earlier data demonstrate that MEK1-ERK1/2 signaling pathway is activated in AC5KO, thus we also examined the effect of Ara-Ade on MEK1-ERK1/2 signaling, in the chronic ISO infusion model. Ara-Ade increased phosphorylation of ERK1/2 and MEK1 (FIG. 5), indicating that Ara-Ade prevents LV dysfunction in chronic ISO infusion through activating MEK1-ERK1/2 pathway.

Figure 6:
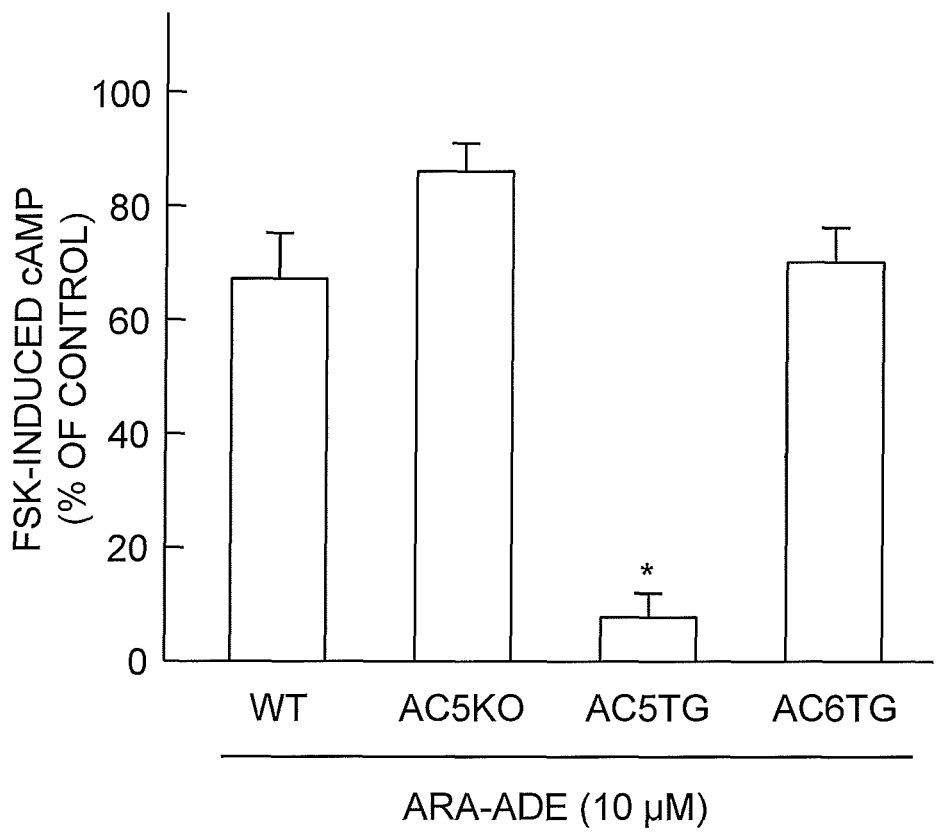
FIG. 6 shows that Ara-Ade inhibits cAMP production in the hearts from AC5Tg, but not AC6Tg suggesting the selectivity of Ara-Ade for AC5, but not AC6. Membrane preparations of the hearts were incubated with $^{32}$P-ATP in the presence of Ara-Ade and forskolin (50 μM), a direct AC stimulator, followed by measuring formed $^{32}$P-cAMP. n=4. *, p<0.01 versus WT.

Recent studies demonstrate the salutary effect of overexpressing AC6, the other major cardiac isoform than AC5, on progression of HF. This indicates that, if Ara-Ade inhibits AC6, administration of Ara-Ade possibly exacerbates HF. Therefore, we examined the effect of Ara-Ade on AC6 activity, using mice with cardiac specific overexpression of AC6 (AC6Tg). As shown in FIG. 6, Ara-Ade inhibited cAMP production in the heart membrane preparation from AC5, but not from AC6, indicating little inhibitory effect of Ara-Ade on AC6.

We examined whether chronic infusion of Ara-Ade increases the survival rate after myocardial infarction. Interestingly, the Ara-Ade administration group showed increased survival rate after a coronary occlusion (FIG. 7a), suggesting that Ara-Ade has salutary effects on the MI heart. Indeed, Ara-Ade rescued MI-induced LV dysfunction (FIG. 7b), indicating that Ara-Ade increases survival rate through protection.

AC5KO Attenuated Aging-Related HF, and Prolonged Longevity.

Figure 8:
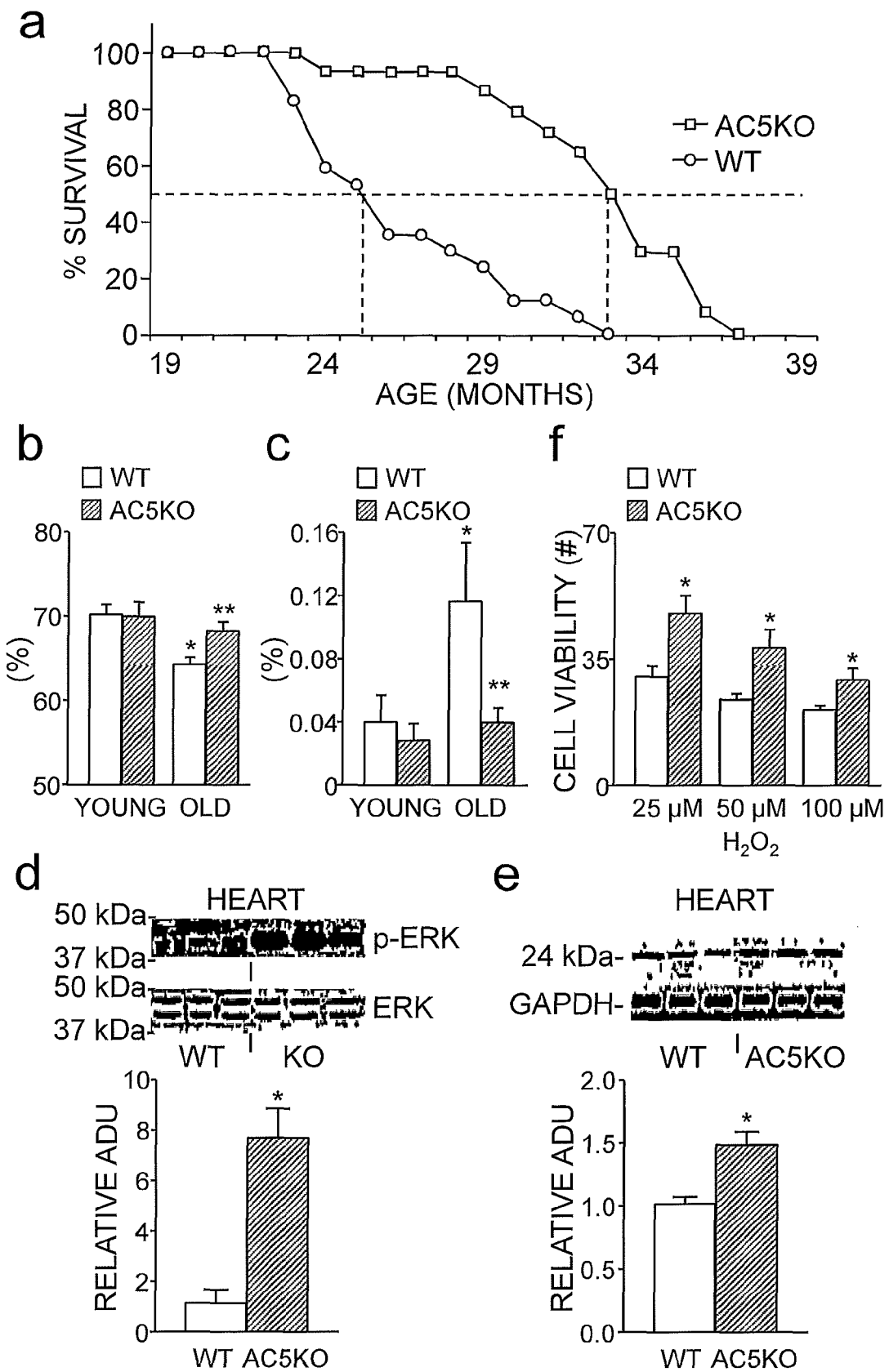
FIG. 8 demonstrates that AC5KO mice show a prolonged life span and resistance to cardiac stress. (a) A retrospective study of WT (n=25) and AC5KO mice (n=13) demonstrated significant differences in longevity between WT and AC5KO. The dotted line indicates the time of 50% survival. Roughly 50% of WT mice died by 25 months, but AC5KO mice died by 33 months. These differences are significant, p<0.01. (b, c) Comparison of LVEF (b) and LV apoptosis (c) in WT and AC5KO, young (3-6 months, n=4-9) and old (20-30 months, n=4-9). *, old WT different from young WT, p<0.05. **, Old AC5KO different from old WT, p<0.05. (d, e) Western blotting of p-ERK, ERK (d) and MnSOD (e) in the heart of WT and AC5KO (20 months, n=4 in each group). The levels of p-ERK and MnSOD are significantly increased in the heart of old AC5KO, *p<0.05. (f) Cell viability was evaluated in response to oxidative stress in neonatal cardiac myocytes. Myocytes were treated with $H_2O_2$ (25, 50, and 100 mM) and evaluated for cell viability using Cell Titer-Blue Cell Viability Assay. AC5KO neonatal myocytes showed more tolerance to oxidative and DNA damage (*p<0.05 versus WT).

Recent data in AC5KO mice demonstrate that deletion of AC5 increased lifespan by ~30% (FIG. 8a). Regarding changes in the hearts of aged mice, old AC5KO mice are also protected from age-related myocardial apoptosis and reduced LV ejection fraction (EF), an indicator of LV contractility (FIGS. 8b and c). ERK, one of the major survival signals in the heart, was markedly activated in AC5KO (FIG. 8d). In addition, the expression of MnSOD, a major anti-oxidant molecule, was significantly increased in AC5KO (FIG. 8e), and cell viability was increased in AC5KO myocytes under oxidative stress (FIG. 8f), indicating that AC5 inhibitors may slow the progression of HF via the regulation of survival signal and oxidative stress. The data from aging hearts in AC5KO animals suggest that AC5 inhibitors may be given to elderly patients, who compose the major population of patients with HF.

HF Model Mice Demonstrated a Crucial Role of AC5 in the Progression of HF.

Figure 9:
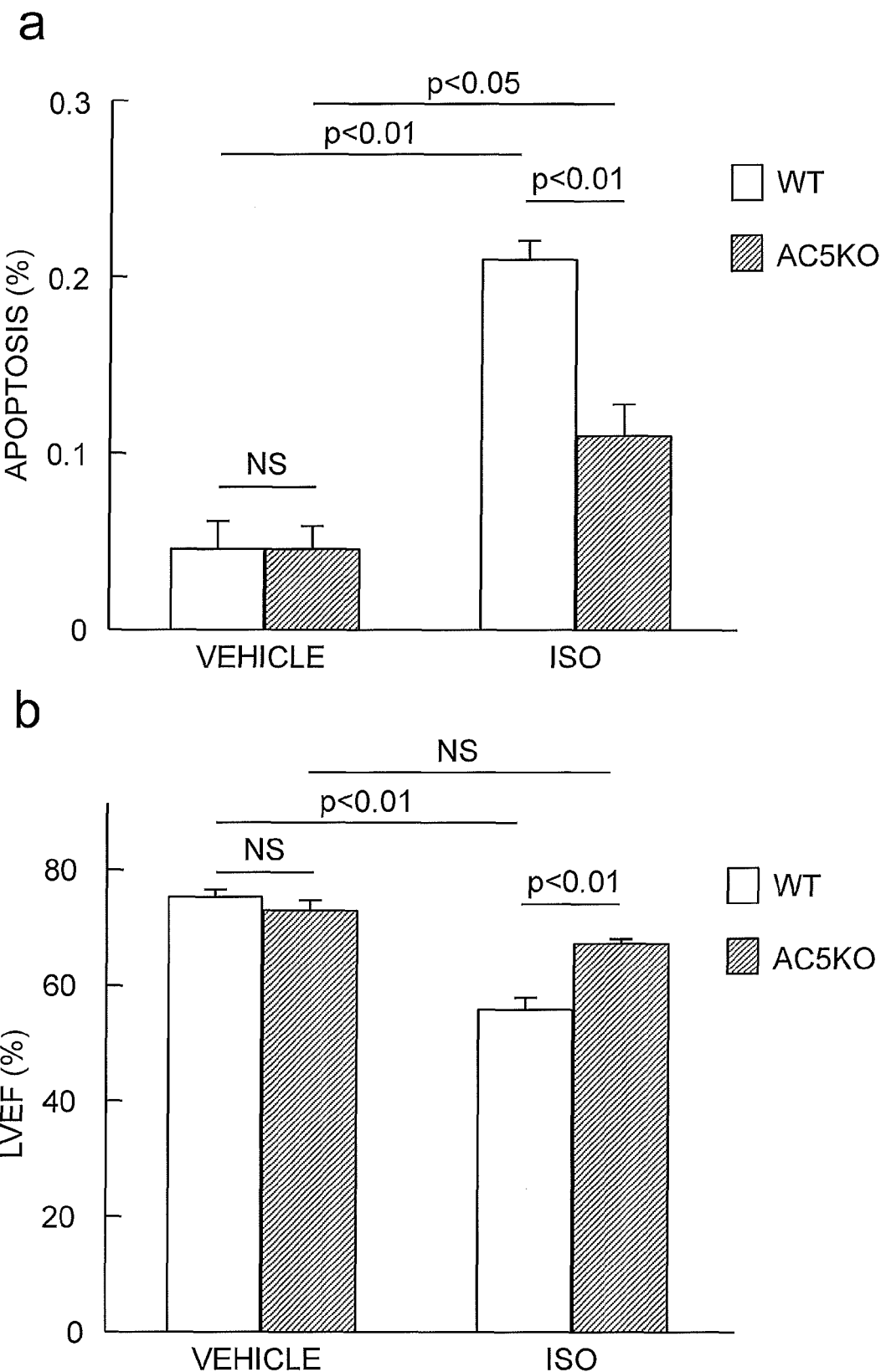
FIG. 9 demonstrates deletion of AC5 attenuated myocardial apoptosis and cardiac dysfunction in 1-week of chronic ISO-infusion HF model. a) Apoptosis was evaluated by Terminal dUTP nick end-labeling (TUNEL) assay. TUNEL-positive myocytes in LV myocardium were counted in WT and AC5KO and are expressed as % of total myocytes. , p<0.01, n=7-10 each. b) Echocardiographic measurements of LV function were performed in WT and AC5KO mice after chronic ISO infusion. LVEF was decreased in both WT and AC5KO after chronic ISO, but the magnitude of the decrease was greater in WT than in AC5KO. p<0.01, n=4-5. Comparisons between multiple groups were made using ANOVA with post-hoc tests.

We compared the effect of chronic infusion of isoproterenol (ISO), a β-AR agonist, which mimics elevated sympathetic activity in HF, between AC5KO and WT mice. Chronic ISO infusion increased myocardial apoptosis in both WT and AC5KO, however, the degree of increase was significantly lower in AC5KO than in WT (FIG. 9a), suggesting that deletion of AC5 attenuated ISO-induced apoptosis. In addition, LVEF was decreased by chronic ISO in both WT and AC5KO, but the magnitude of the decrease was significantly greater in WT than in AC5KO (FIG. 9b), indicating that deletion of AC5 attenuated the deterioration of cardiac function.

Figure 10:
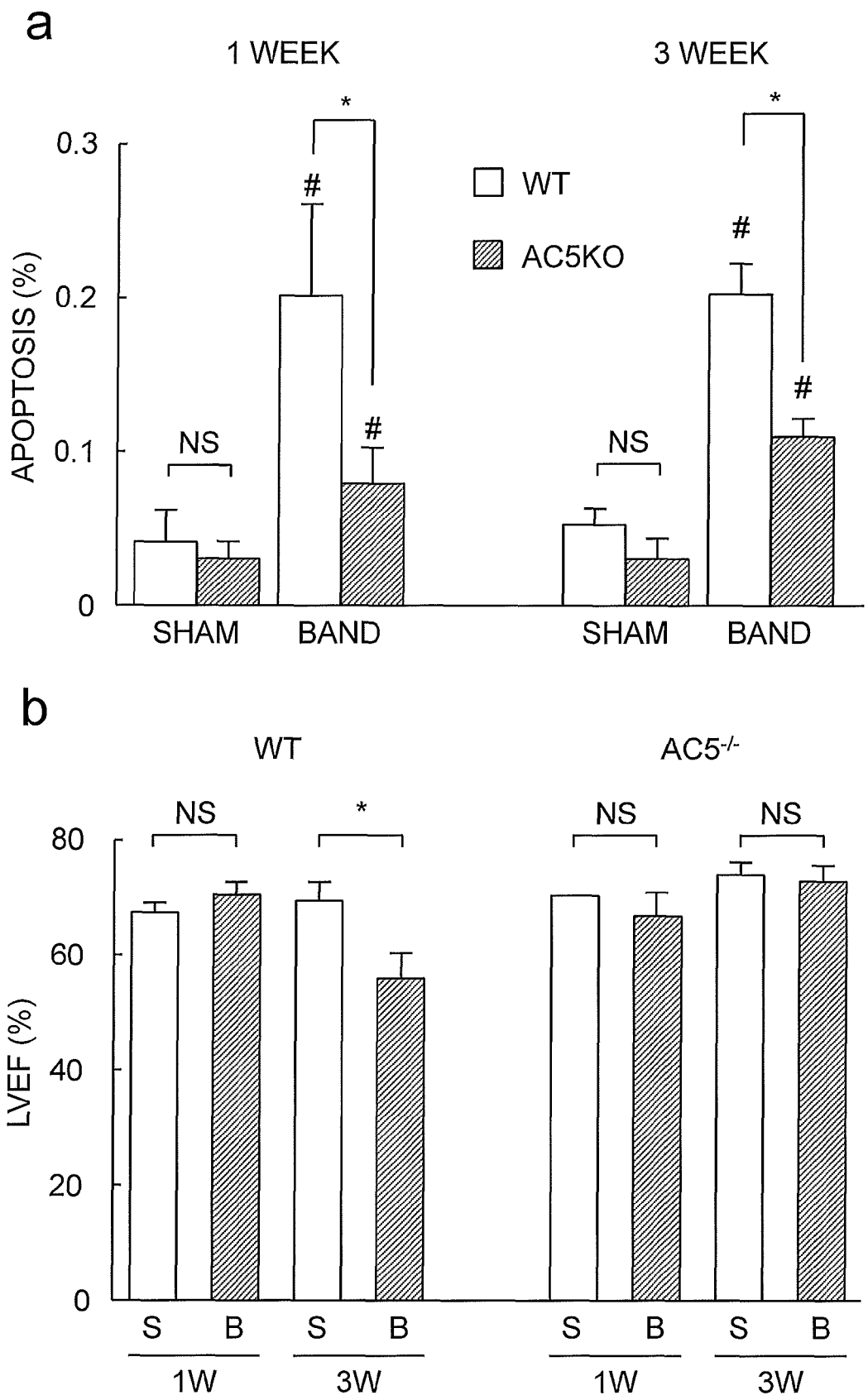
FIG. 10 demonstrates that deletion of AC5 attenuates myocardial apoptosis and maintains cardiac function in aortic banded mice. a) Apoptosis was evaluated with a TUNEL assay. TUNEL-positive myocytes in LV myocardium were counted in WT and AC5KO mice and are expressed as % of total myocytes. The number of TUNEL-positive myocytes is significantly smaller in AC5KO mice than in WT mice after either 1 or 3 weeks of banding (n=6 each). *, p<0.05. #, p<0.05 vs. sham. b) Echocardiographic measurements of LVEF were performed in WT and AC5KO mice after 1 and 3 weeks of banding. The data (B, banding) were compared with those from sham-operated (S) controls. LVEF was significantly decreased after 3 weeks of banding in WT but not in AC5KO. *, p<0.05. Comparisons between multiple groups were made using ANOVA with post-hoc tests.

In addition to the chronic ISO infusion HF model, AC5KO mice also exhibited decreased myocardial apoptosis and attenuated LV dysfunction in a pressure overload HF model induced by aortic banding. Aortic banding increased myocardial apoptosis in both WT and AC5KO, although the increase in apoptosis was smaller in AC5KO than in WT (FIG. 10a). In addition, after 3 weeks of aortic banding, LVEF was significantly decreased in WT while it remained unchanged in AC5KO, when compared to sham-operated mice (FIG. 10b). These results suggested that AC5 inhibitors would attenuate apoptosis and the progression of HF in this model.

Moreover, mice with cardiac specific overexpression of AC5 (AC5Tg) mice, showed increased myocardial apoptosis and decreased LVEF in both chronic ISO infusion HF model, indicating that AC5 increases myocardial apoptosis and accelerates the progression of HF. Therefore, pharmacological inhibition of AC5 attenuates myocardial apoptosis and the progression of HF.

Drugs with Adenosine-Like Structure have an AC5 Inhibitory Effect.

Figure 11:
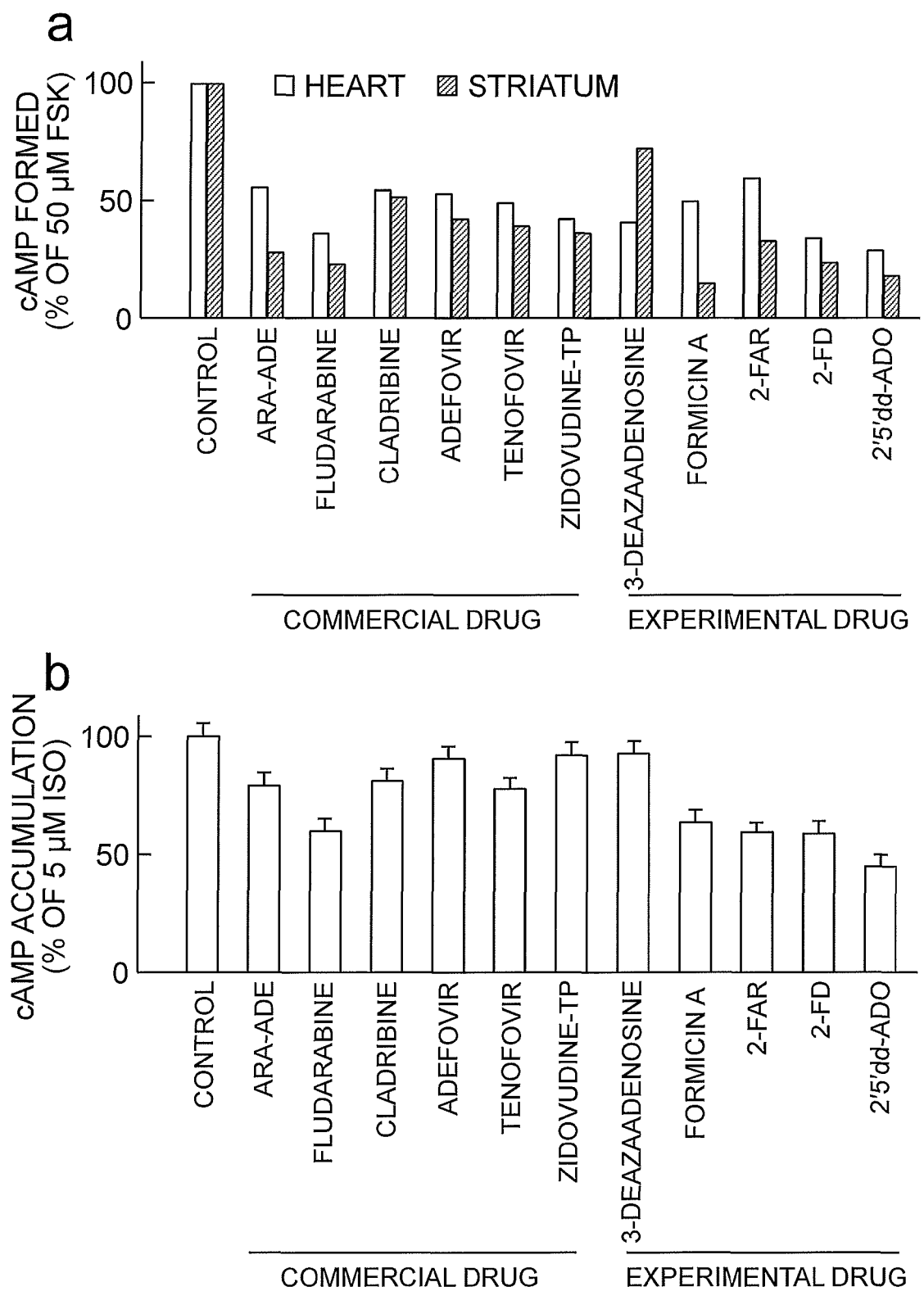
FIG. 11 demonstrates some known AC5 inhibitors. a) cAMP formation was performed in membrane preparations from the striatum, in which AC5 provides 80% of total AC activity, and the heart, in which AC5 provides 20% of total AC activity. n=3. b) cAMP accumulation was examined in H9C2 cells, a cardiac myoblast cell line. n=4.

To find more potent AC5 inhibitors than Ara-Ade, drugs with the adenosine-like structure, which is required for binding to and inhibition of AC, were tested. Several approved and experimental drugs that show AC5 inhibition were found (FIG. 11a). Since the catalytic site of AC is in the intracellular domain, the plasma membrane permeability of these drugs using H9C2, a cardiac myoblast cell line was examined (FIG. 11b). These inhibitors also show AC inhibition in H9C2, suggesting that these drugs exert the AC inhibitory effects when administered to intact cells. Among these inhibitors, fludarabine, an anti-leukemia drug, showed more potent inhibition of AC5 and cAMP accumulation than Ara-Ade; however, fludarabine is known to have severe adverse effects including bone marrow suppression which occur in roughly half of administered patients.

To measure AC5 inhibition, in addition to membrane preparations from mouse heart, we also used membrane preparations from mouse striatum because AC5 provides about 80% of total AC activity in the striatum; accordingly, this membrane preparations mimics purified AC5, but does not reflect membrane-permeability of drugs. Such membrane permeability was examined using whole cell, which is addressed in FIG. 11b). cAMP production was measured with 50 μM forskolin in the presence or absence of 10 μM of the indicated drugs. n=2. (b) cAMP accumulation is shown in H9C2 cells. Cells were stimulated with 5 μM isoproterenol (ISO), a β-AR agonist, for 3 minutes in the presence or absence of the indicated drugs (10 μM). Ara-Ade (Adenine 9-β-D-arabinofuranoside) is an anti-herpes simplex drug. Fludarabine ((+)-2-Fluoro-9-(5-O-phosphono-β-D-arabinofuranosyl)-9H-purin-6-amine) and Cladribine (2-chloro-2'-deoxyadenosine) are anti-cancer drugs, Adefovir (Bis(2,2-dimethylpropanoyloxymethyl))[2-(6-amino-9H-purin-9-yl) ethoxymethyl]phosphonate) and Zidovudine are anti-HIV drugs. Zidovudine-TP is a metabolite of zidovudine which inhibits virus replication. TP; triphosphate. 3-Deazaadenosine, Formycin A (7-Amino-3-(β-D-ribofuranosyl)-1H-pyrazolo[4,3-d]pyrimidine), 2-Far (2-Fluoroadenosine), formycin A ((2S,3R,4S,5R)-2-(7-amino-2H-pyrazolo[5,4-e]pyramidin-3-yl-5-(hydroxymeth-yl)oxolane-3,4-diol), 2-FD (2-Fluoro-2'-deoxyadenosine) and 2'5' ddAdo (2'5'-dideoxyadenosine) are experimental drugs.

AC5 Inhibitors Inhibit β-AR-Induced Apoptosis without Deteriorating Contraction in Cultured Cardiac Myocytes.

AC5 inhibitors attenuate apoptosis without deteriorating contraction in cultured cardiac myocytes. AC5 inhibitors, such as 2'5'-dideoxyadenosine (2'5'-dd-Ado), Ara-Ade and 1R,4R-3-(6-amino-purin-9-yl)-cyclopentanecarboxylic acid hydroxyamide (PMC-6), abolished ISO-induced apoptosis in cultured cardiac myocytes (FIG. 3d). Cultured cardiac myocytes from AC5KO were protected against ISO-induced apoptosis (FIG. 3c). In contrast, although 10 μM PMC-6 decreased ISO-induced cAMP production (FIG. 3b) by 50%, it did not inhibit ISO-induced cell contraction (data not shown), indicating that activation of AC5 did not affect contractility. In addition, apoptosis was induced at a high ISO concentration (100 μM) (FIG. 3d), whereas contraction almost reached a peak at a low ISO concentration (10 nM) (data not shown), suggesting that AC5 is only stimulated by high ISO concentration, i.e., strong (β-AR stimulation which occurs in elevated sympathetic activity with HF, but not in normal sympathetic activity. Indeed, cAMP in AC5KO was decreased at a high concentration of ISO (1 μM) (FIG. 3e), suggesting that AC5 is only activated by strong β-AR stimulation. Ara-Ade shows un- or non-competitive with respect to ATP (FIG. 3e), suggesting that Ara-Ade hardly affects binding of molecules within the ATP binding site.

AC5 Inhibitors Inhibited Myocardial Apoptosis and HF in the Chronic ISO Infusion Model.

Figure 12:
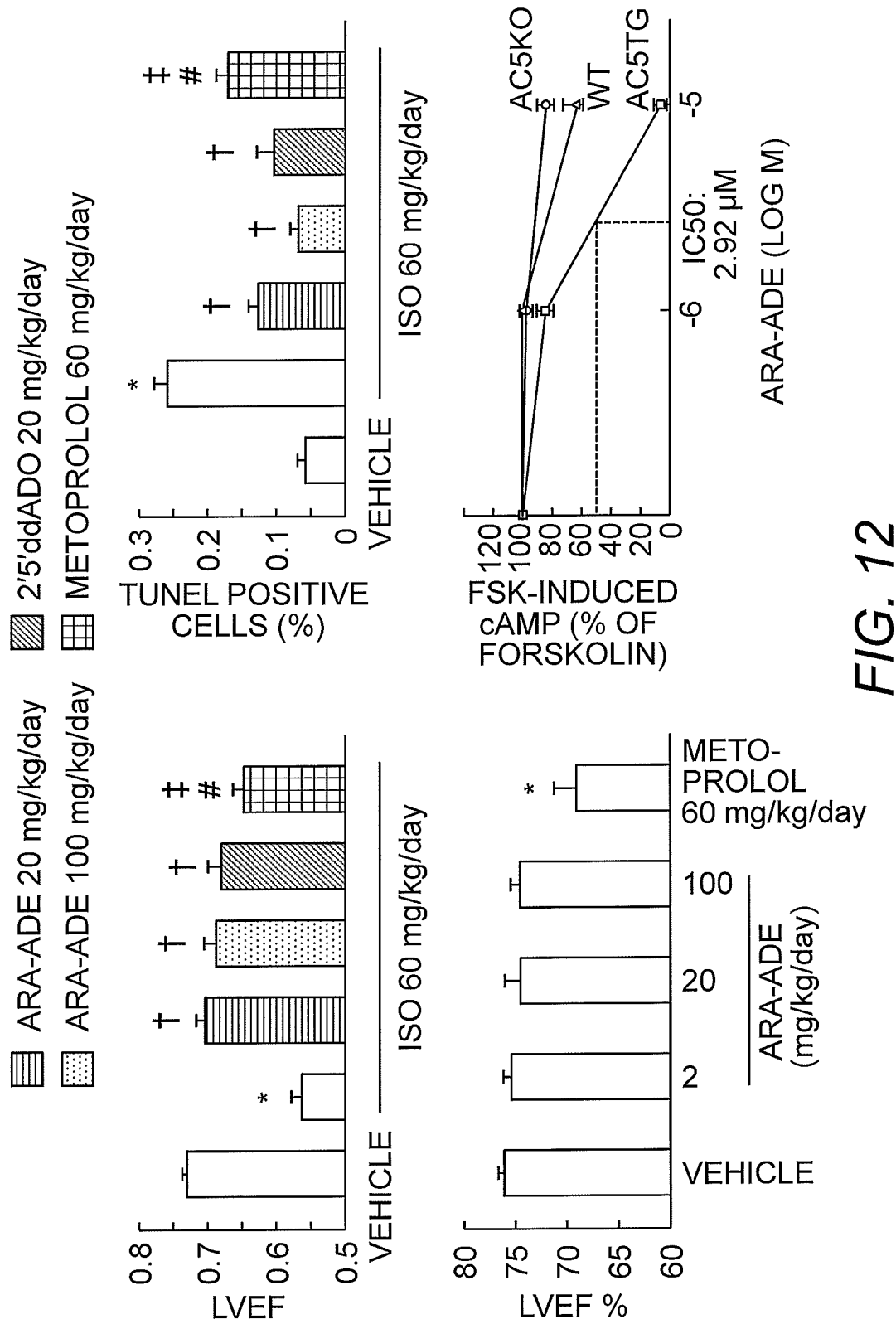
FIG. 12 demonstrates that AC5 inhibitors attenuate cardiac myocyte apoptosis and cardiac dysfunction induced chronic ISO infusion. In C57Bl/6 mice, ISO with or without AC5 inhibitors or metoprolol were chronically infused with an osmotic mini-pump at the indicated doses for 1 week. Mice were then subjected to echocardiography (a) and heart tissue were subjected to a myocardial apoptosis assay (b). *, p<0.01 vs vehicle. #, p<0.05 vs vehicle. .dagger., p<0.01 vs ISO. .dagger-dbl., p<0.05 vs ISO. n=4-15. (c) Chronic infusion of Ara-Ade for 1 week did not change LVEF in mice, but metoprolol decreased. *, p<0.01 vs vehicle. n=5-7. e) cAMP production in the hearts from WT, AC5KO and AC5Tg was measured with forskolin (50 μM), a direct AC stimulator in the presence or absence of followed by measuring formed $^{32}$P-cAMP. n=4. *, p<0.01 versus WT. Comparisons between multiple groups were made using ANOVA with post-hoc tests.
Figure 13:
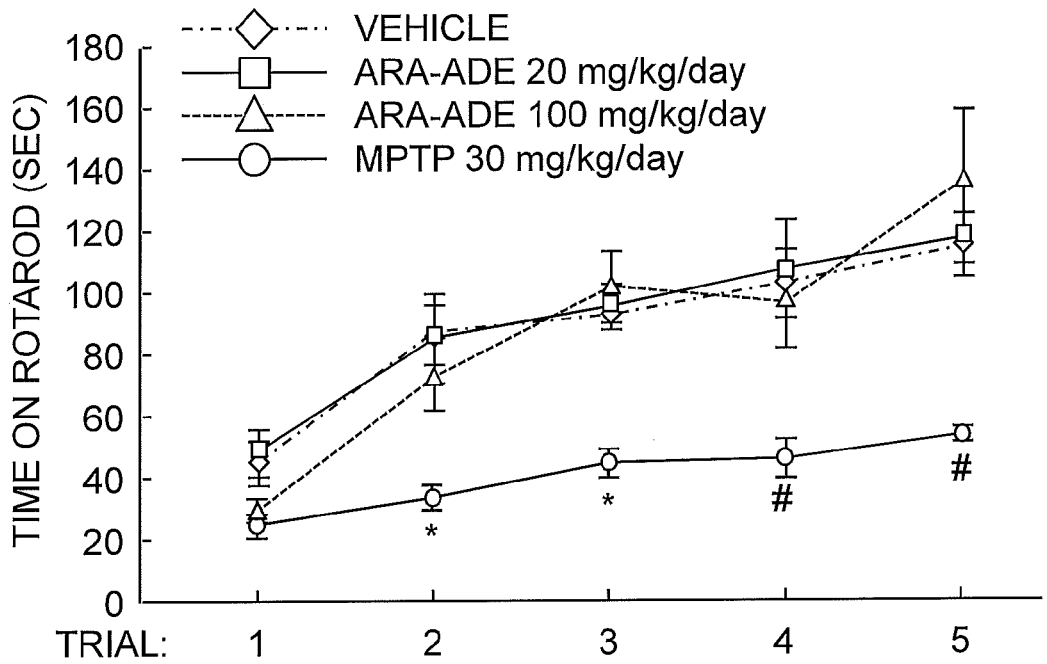
FIG. 13 demonstrates that Ara-Ade does not affect motor function. In C57Bl/6 mice, Ara-Ade was chronically infused with an osmotic mini-pump at the indicated doses for 5 days. a) Each mouse was placed on a rod subjected to evaluate Rotarod performance. Mice were left for 1 min on the rod for habituation. The rod rotated gradually increasing from 4 to 40 rpm over the course of 5 min, and the time that mice could stay without failing was recorded. Five trials were conducted for each individual 10-25 min apart. As a positive control, 1-methyl 4-phenyl 1,2,3,6-tetrahydropyridine (MPTP) was intraperitoneally injected for the indicated dose for 5 days. *, p<0.01 relative to vehicle. #, p<0.05 relative to vehicle. n=6-7. b) To evaluate bradykinesia, a pole test was performed. Mice were placed head upward on the top of a rough surfaced pole that was wrapped with gauze to prevent slipping. The time until the mouse turned completely downward (open bars, TTURN) and the time until it climbed down to the floor (closed bars, TLA) were measured.
Figure 13:
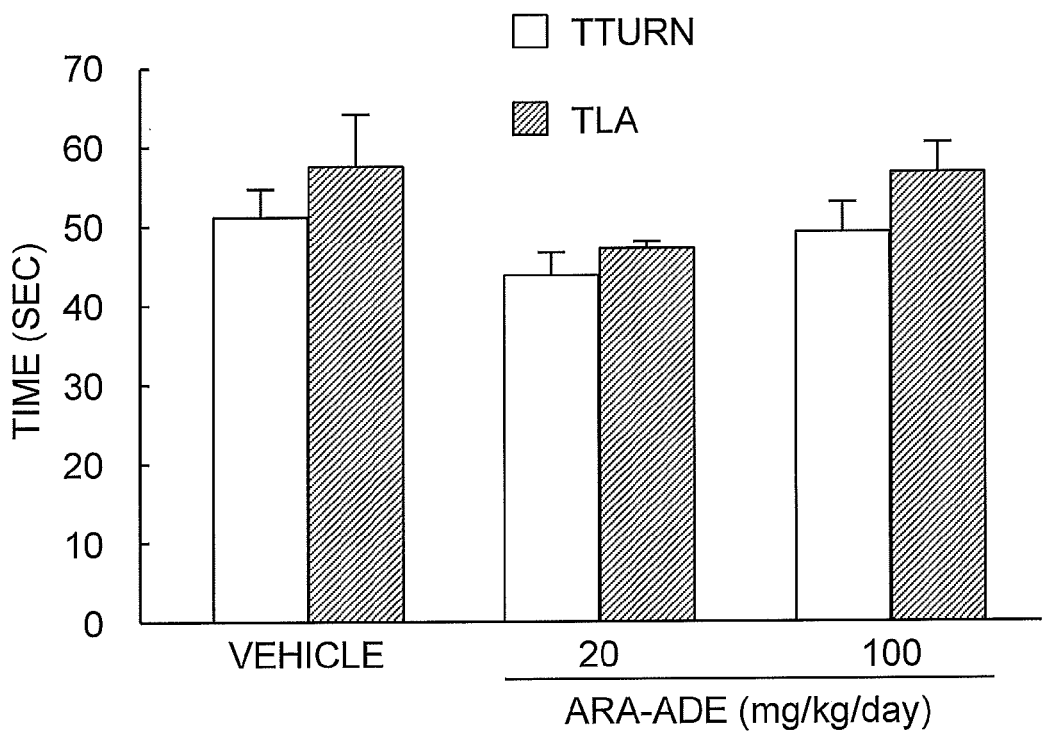

To examine the effect of Ara-Ade on HF, the effects of the AC5 inhibitors, Ara-Ade and 2'5' ddAdo were tested in a model of HF induced by chronic ISO infusion. Ara-Ade and 2'5' ddAdo inhibited the ISO-induced LVEF decrease (FIG. 12a). In addition, Ara-Ade and 2'5' ddAdo significantly inhibited ISO-induced myocardial apoptosis and fibrosis (FIGS. 12b and 13c), indicating that these AC5 inhibitors exert their effects even in vivo. On the other hand, chronic Ara-Ade infusion did not affect basal LVEF (FIG. 12d), this is consistent with the data in AC5KO such that basal LVEF is similar between AC5KO and WT mice. Chronic infusion of metoprolol, an established β-blocker was examined in a chronic ISO infusion model, metoprolol attenuated ISO-induced cardiac dysfunction; however, the degree was less than Ara-Ade (FIG. 12a). This is partially attributable to attenuation in LVEF by metoprolol (FIG. 12c). Also, metoprolol attenuated ISO-induced myocardial apoptosis to a lesser degree than Ara-Ade. This indicates that at the dose which attenuates LVEF, the anti-apoptosis effect of metoprolol is weaker than that of Ara-Ade, i.e., metoprolol is less effective on AC5 inhibition than Ara-Ade. Altogether, these data supports our idea that Ara-Ade might be an superior alternative to a existing β-blockers.

In addition, the concentration of Ara-Ade used (20 mg/kg/day) is slightly higher than that used clinically to treat systemic Herpes Simplex infection (15 mg/kg/day) in the past. When injected IV (10 mg/kg, intravenously infusion for 30 min), Ara-Ade Cmax in human is 4.8 This is similar to the effective concentration in inhibiting apoptosis (10 μM, FIG. 3d). In addition, $IC_{50}$ for recombinant AC5 is 9.8 μM and $IC_{50}$ for forskolin-stimulated cAMP production in membrane preparations from the heart of AC5Tg animals is 2.92. Therefore, Ara-Ade may attenuate AC5 activity in the heart when administered at the dose of 15 mg/kg/day.

Ara-Ade Inhibits AC5 but Not AC6.

Recent studies demonstrate the salutary effect of overexpressing AC6, the other major AC cardiac isoform, on progression of HF. This indicates that if Ara-Ade inhibits AC6, it should exacerbate HF. The effect of Ara-Ade on AC6 activity was examined using mice with cardiac specific overexpression of AC6 (AC6Tg). As shown in FIG. 6, Ara-Ade inhibited cAMP production in the heart membrane preparation from AC5, but not from AC6, indicating little inhibitory effect of Ara-Ade on AC6.

Ara-Ade does Not Affect Motor Function

AC5 mainly expresses in the striatum other than the heart, and inhibiting AC5 in the striatum resulted in impaired motor function as observed in AC5KO. Thus, the effect of chronic infusion of Ara-Ade on motor function was examined. Rotarod performance and pole test, which detect abnormalities in coordinated movement and bradykinesia, respectively, were examined. In addition, both were impaired in AC5KO mice. As shown in FIGS. 11a and 11b, chronic infusion of Ara-Ade does not show abnormalities in these tests. This indicates that Ara-Ade has little adverse effects in brain function when administered, and demonstrates that Ara-Ade has little BBB-permeability.

Ara-Ade Reduces Infarct Size and Limits Reperfusion Injury

The rescue of cardiac cells from death after an ischemic injury is a major goal of reperfusion therapy. A quick mechanical or pharmacological intervention to open an occluded coronary artery is crucial to rescue the heart from this injury. Beyond that, however, additional therapies to reduce infarct size and limit reperfusion injury are largely lacking. Most, if not all, cardioprotective molecules are effective when given before an ischemic event but not during or after reperfusion relief. This is perhaps the most important limitation to success with respect to these other cardioprotective molecules on limiting infarct size in patients, since such compounds are only effective when given before the myocardial infarction or at least before reperfusion. Since patients come to the hospital with a coronary artery occluded and the physician is not going to wait to open up the artery and reperfuse (time of coronary occlusion is directly related to infarct size), it is not feasible to administer an agent that only works before reperfusion.

Figure 14:
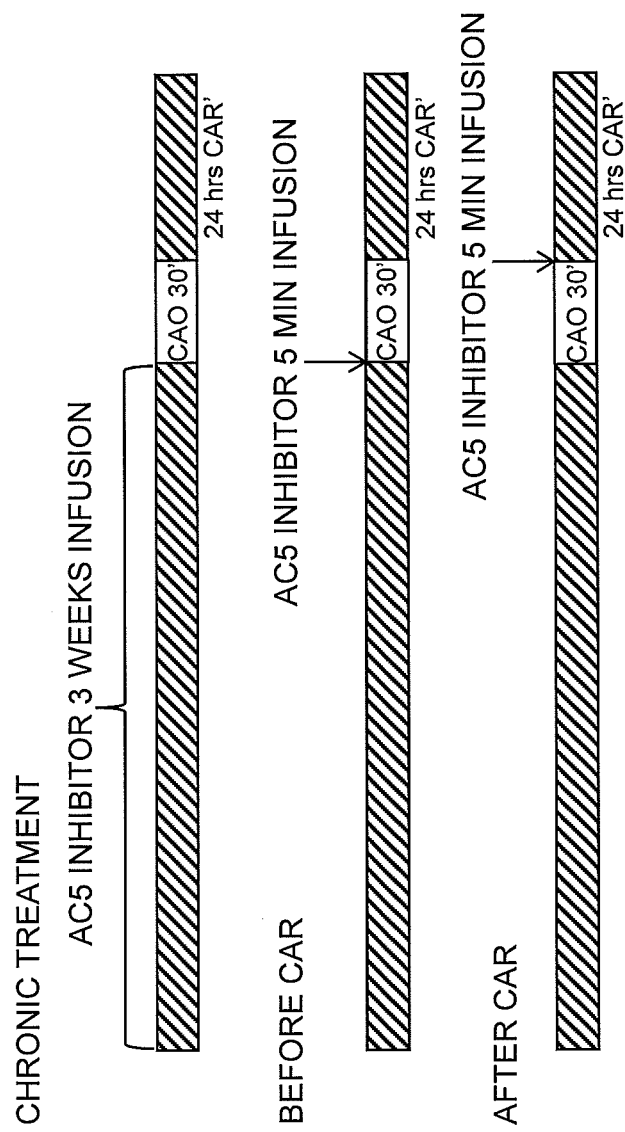
FIG. 14 shows the protocols used to demonstrate effectiveness of the AC5 inhibitor Ara-Ade in reducing infarct size more effectively when given during or after coronary artery reperfusion (CAR) than before CAR in mice with coronary artery occlusion (CAO). Mice were divided into three different groups. Group I was administered AC5 inhibitor chronically for three weeks prior to CAO for 30 minutes followed by CAR for 24 hours. Group II was administered the AC5 inhibitor by i.v. infusion for 5 minutes immediately prior to CAO for 30 minutes followed by CAR for 24 hours. Group III was administered the AC5 inhibitor by i.v. infusion for 5 minutes immediately following CAO for 30 minutes and during CAR for 24 hours. Vehicle controls were included for all three treatment groups.
Figure 15A:
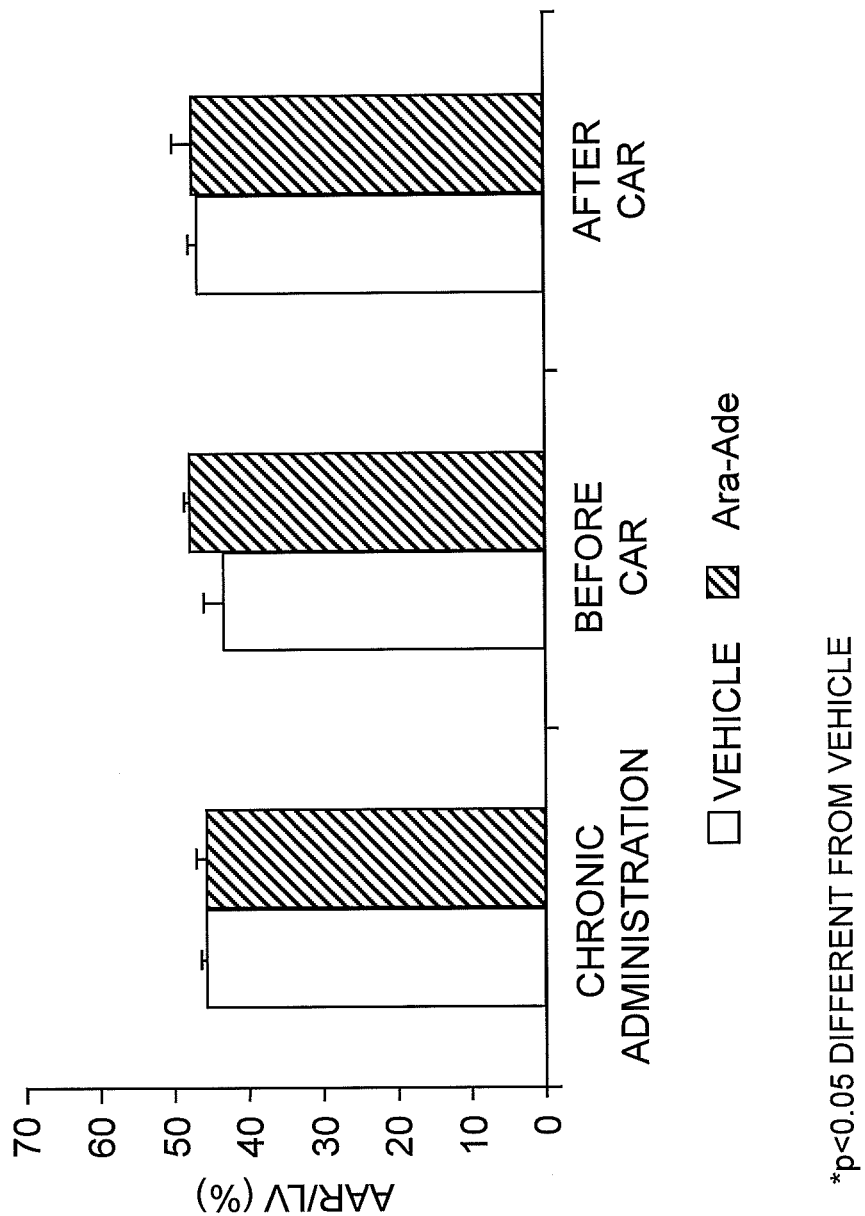
FIG. 15(a-b) demonstrates that while the area of risk in coronary artery occluded mice was similar in all three treatment Groups described in FIG. 14 (see FIG. 15a), the AC5 inhibitor Ara-Ade reduced infarct size more effectively when administered after CAO during or after CAR than before CAO either chronically or by i.v. infusion.
Figure 15B:
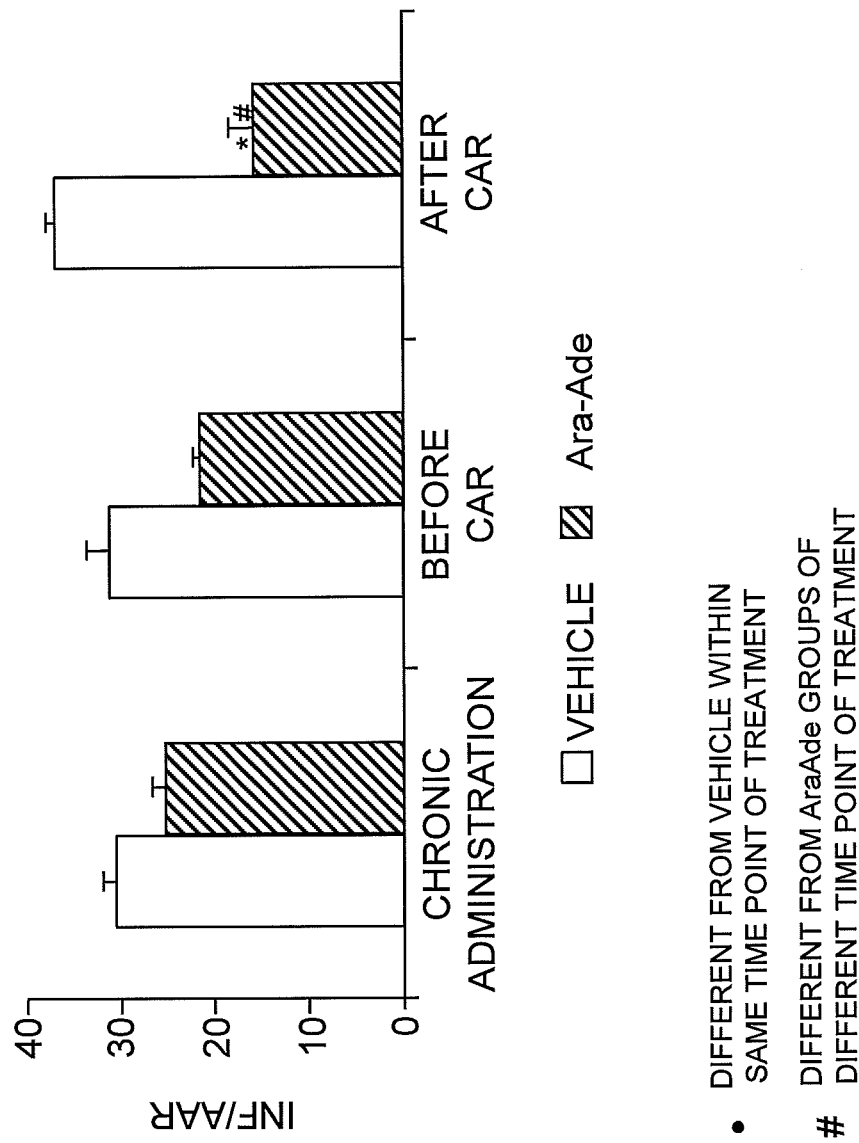
Figure 16:
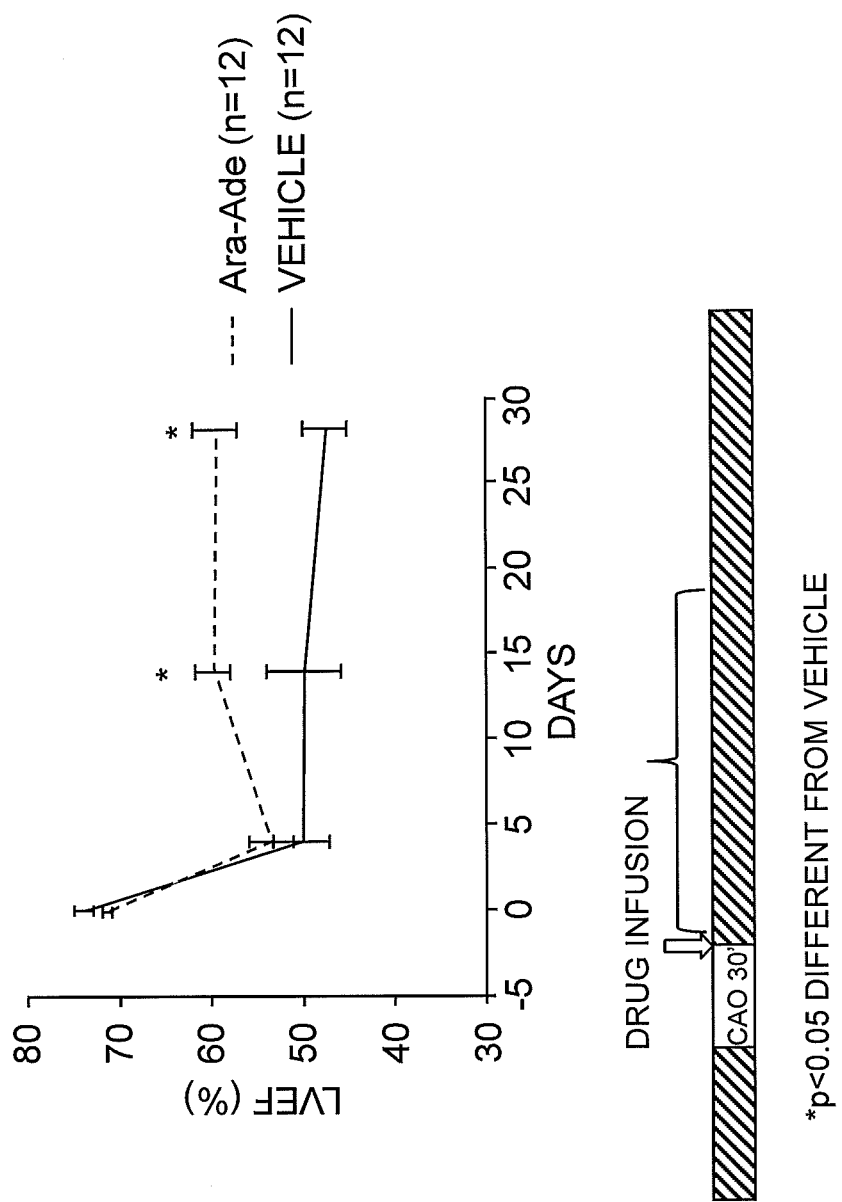
FIG. 16 demonstrates that administration of the AC5 inhibitor Ara-Ade to mice by i.v. infusion after CAO and during or after CAR also prevented the development of heart failure.

We examined the ability of the AC5 inhibitor Ara-Ade to reduce infarct size when administered after 30 min Coronary Artery Occlusion (CAO) and during or after 24 hr Coronary Artery Reperfusion (CAR) in mice (See FIG. 14). Unexpectedly and significantly, infarct size was lower when the drug was delivered after CAO and/or CAR, as compared to drug administered before CAO (See FIG. 15b). Further, Ara-Ade did not reduce arterial pressure and reflexly increase heart rate as many other cardioprotective agents do, e.g. the structurally similar cardioprotective molecule adenosine (See FIG. 1). As shown in FIG. 16, administration of the AC5 inhibitor after CAR and during or after reperfusion also prevented development of heart failure in mice.

Figure 17B:
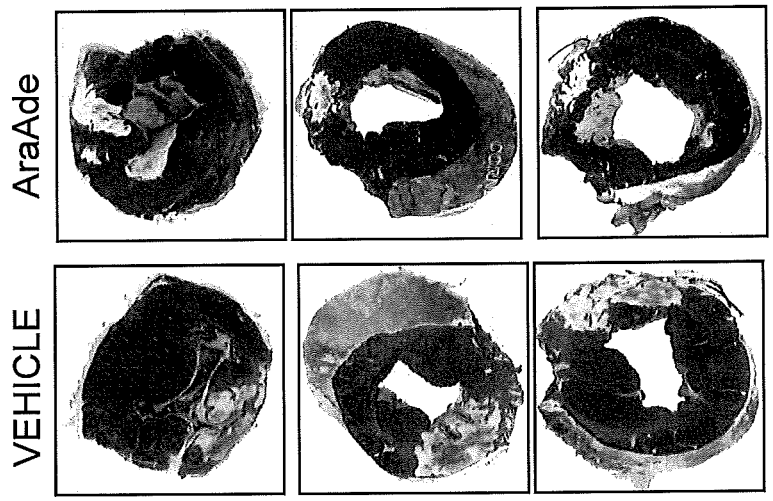
FIG. 17(a-b) demonstrates the ability of the AC5 inhibitor Ara-Ade to reduce infarct size in the larger mammalian pig model as well. In these experiments, Ara-Ade was administered after CAO through an indwelling left anterior descending coronary catheter to conscious, chronically instrumented pigs.
Figure 17A:
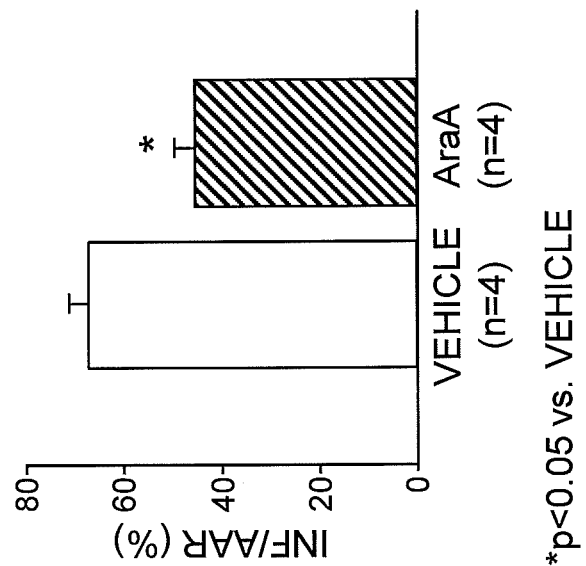
Figure 18A:
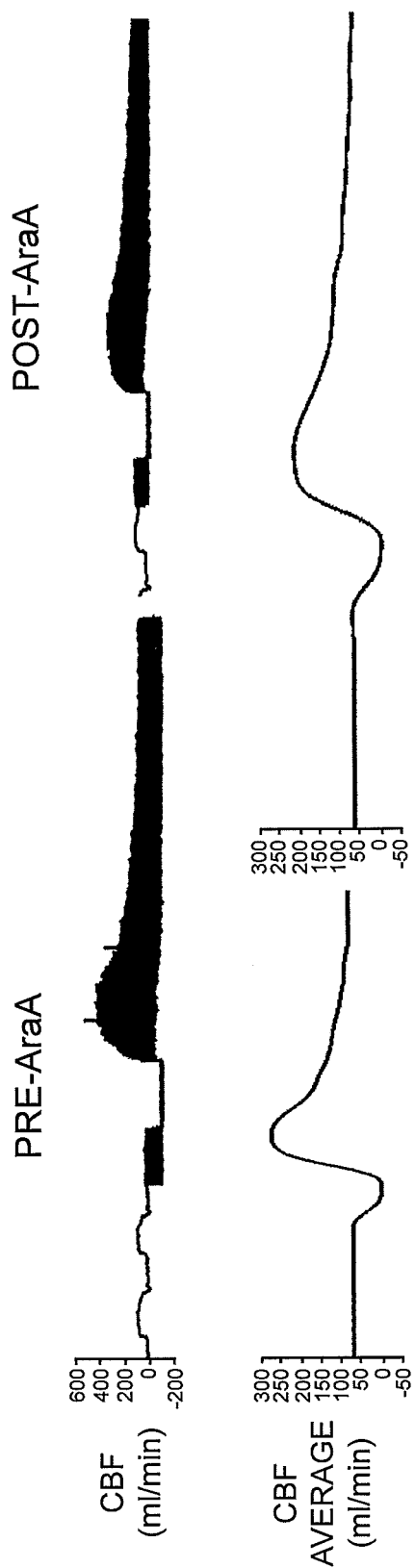
FIG. 18(a-b) demonstrates the ability of the AC5 inhibitor Ara-Ade to inhibit hyperemia when administered after CAO through an indwelling left anterior descending coronary catheter to conscious, chronically instrumented pigs.
Figure 18B:
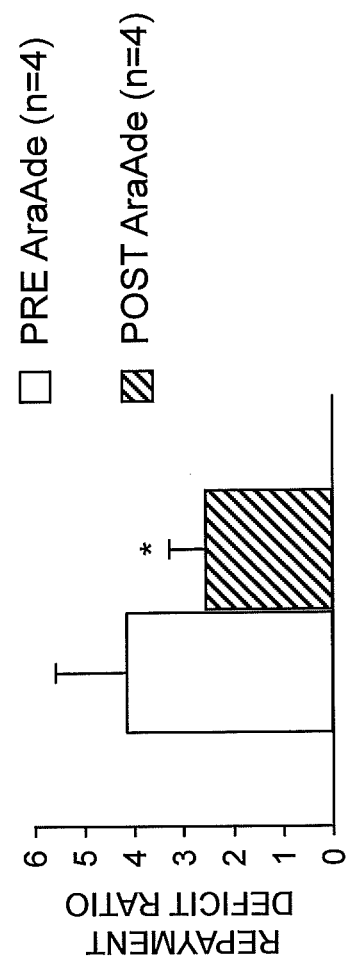

In order to translate this drug to patients, effectiveness of the AC5 inhibitor was also evaluated in the larger mammalian pig model. As shown in FIGS. 17a and 17b, Ara-Ade reduced infarct size in chronically instrumented conscious pigs when delivered after CAR. Interestingly, Ara-Ade inhibited reactive hyperemia in the pigs, a mechanism believed to be important in limiting oxidative stress that contributes to reperfusion injury (See FIG. 18a and FIG. 18b).

This combination of properties, especially, the fact that these compounds are more effective when given at the time of coronary reperfusion or after reperfusion, combined with existing FDA approval for Ara-Ade, makes this drug, as well as other AC5 inhibitors, particularly useful in limiting ischemic injury following myocardial infarction in patients.

While compounds useful in this aspect of the present invention relating to reducing infarct size and/or limiting, decreasing and/or inhibiting reperfusion injury in a patient inhibit AC5, this may not be the main mechanism of action by which they reduce infarct size after reperfusion. While not being limited in any way to a particular mechanism, it is believed that similarity in structure to adenosine (See FIG. 1) and the ability of these compounds to activate the adenosine receptor may be responsible for the ability of these AC5 inhibitors to reduce infarct size. Unlike adenosine and adenosine like compounds which have failed in clinical trials, in many cases due to their adverse effects on arterial pressure and heart rate, however, we have found that AC5 inhibitors used in accordance with the present invention have a very weak effect on vasodilation. Accordingly, AC5 inhibitors do not change arterial pressure and heart rate, thus making these drugs more beneficial to patients with myocardial infarction, where a drop in pressure will exacerbate the infarction. We also found in the pig that the AC5 inhibitors reduce the hyperemia after reperfusion and reduce reactive hyperemia, i.e., opposite to an adenosine action. This is important because the hyperemia that follows reperfusion has been implicated in the mechanism for reperfusion damage due to oxidative stress, which increases infarct size.

Accordingly, for this aspect of the present invention involving reduction in infarct size and/or limiting, decreasing and/or inhibiting reperfusion injury, the compound capable of inhibiting AC5 administered to the patient may be similar in structure to adenosine. In some embodiments, the AC5 inhibiting compound is 9-β-D-arabinofuranosyladenine (Ara-Ade). For this aspect of the present invention, when administering an AC5 inhibitor such as Ara-Ade, the compound may be administered in an amount far lower, for example less that 1 mg/kg, less than 0.1 mg/kg, or about 0.06 mg/kg, than the antiviral doses of 10-30 mg/kg used in humans. In this embodiment, the compound can be administered as a single i.v. infusion. Further, for this aspect of the present invention, in most embodiments the compound is administered during or after reperfusion following an ischemic injury such as, but not limited to, myocardial infarction and Acute Coronary Syndrome. The AC5 inhibitor may be administered singly or in combination with another agent, such as, for instance a β-blocker.

Formulations and Methods of Administration

A pharmaceutical composition useful in the present invention comprises an AC5 inhibitor and a pharmaceutically acceptable carrier, excipient, diluent and/or salt.

Pharmaceutically acceptable carrier, diluent, excipient and/or salt means that the carrier, diluent, excipient and/or salt must be compatible with the other ingredients of the formulation, does not adversely affect the therapeutic benefit of the AC5 inhibitor, and is not deleterious to the recipient thereof.

Administration of the compounds or pharmaceutical compositions thereof for practicing the present invention can be by any method that delivers the compounds systemically. These methods include oral routes, parenteral routes, intraduodenal routes, etc.

For topical applications, the compound or pharmaceutical composition thereof can be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax, sugars such as lactose and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Depending on the particular condition, disorder or disease to be treated, additional therapeutic agents can be administered together with the AC5 inhibitor. Those additional agents can be administered sequentially in any order, as part of a multiple dosage regimen, from the AC5 inhibitor-containing composition (consecutive or intermittent administration). Alternatively, those agents can be part of a single dosage form, mixed together with the AC5 inhibitor in a single composition (simultaneous or concurrent administration).

For oral administration, a pharmaceutical composition useful in the invention can take the form of solutions, suspensions, tablets, pills, capsules, powders, granules, semisolids, sustained release formulations, elixirs, aerosols, and the like. Tablets containing various excipients such as sodium citrate, calcium carbonate and calcium phosphate are employed along with various disintegrants such as starch, preferably potato or tapioca starch, and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof. The choice of formulation depends on various factors such as the mode of drug administration (e.g., for oral administration, formulations in the form of tablets, pills or capsules are preferred) and the bioavailability of the drug substance.

A suitable pharmaceutical composition for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Aqueous solutions are especially suitable for intravenous, intramuscular, subcutaneous and intraperitoneal injection purposes. In this connection, the sterile aqueous media employed are all readily obtainable by standard techniques well-known to those skilled in the art. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The pharmaceutical compositions useful in the present invention can also contain adjuvants such as, but not limited to, preservatives, wetting agents, emulsifying agents, and dispersing agents. Prevention of the action of microorganisms can be ensured by the inclusion of various antibacterial and antifungal agents, such as for example, paraben, chlorobutanol, phenol sorbic acid, and the like. It can also be desirable to include isotonic agents such as sugars, sodium chloride, and the like. Prolonged absorption of the injectable pharmaceutical form can be brought about by the inclusion of agents that delay absorption such as aluminum monostearate and gelatin.

Injectable depot forms are made by forming microencapsule matrices of the drug in biodegradable polymers such as polylactide, polyglycolide, and polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

For purposes of transdermal (e.g., topical) administration, dilute sterile, aqueous or partially aqueous solutions (usually in about 0.1% to 5% concentration), otherwise similar to the above parenteral solutions, are prepared.

The pharmaceutical compositions useful in the invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

In nonpressurized powder compositions, the active ingredients in finely divided form can be used in admixture with a larger-sized pharmaceutically acceptable inert carrier comprising particles having a size, for example, of up to 100 µm in diameter. Suitable inert carriers include sugars such as lactose. Desirably, at least 95% by weight of the particles of the active ingredient have an effective particle size in the range of 0.01 to 10 µm.

Alternatively, the composition can be pressurized and contain a compressed gas, such as, e.g., nitrogen, carbon dioxide or a liquefied gas propellant. The liquefied propellant medium and indeed the total composition are preferably such that the active ingredients do not dissolve therein to any substantial extent. The pressurized composition can also contain a surface active agent. The surface active agent can be a liquid or solid non-ionic surface active agent or can be a solid anionic surface active agent. It is preferred to use the solid anionic surface active agent in the form of a sodium salt.

Compositions for rectal or vaginal administration are preferably suppositories which can be prepared by mixing the compounds of the invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions useful in the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the invention, stabilizers, preservatives, excipients, and the like. The preferred lipids are the phospholipids and the phosphatidyl cholines (lecithins), both natural and synthetic. Methods to form liposomes are known in the art (e.g., Prescott, E., Meth. Cell Biol. 14:33 (1976)).

Other pharmaceutically acceptable carrier includes, but is not limited to, a non-toxic solid, semisolid or liquid filler, diluent, encapsulating material or formulation auxiliary of any type, including but not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Solid pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients can be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Methods of preparing various pharmaceutical compositions with a certain amount of active ingredient are known, or will be apparent in light of this disclosure, to those skilled in this art. Other suitable pharmaceutical excipients and their formulations are described in Remington's Pharmaceutical Sciences, edited by E. W. Martin, Mack Publishing Company, 19th ed. (1995).

Pharmaceutical compositions useful in the present invention can contain 0.1%-95% of the compound(s) of this invention, preferably 1%-70%. In any event, the composition or formulation to be administered will contain a quantity of a compound(s) according to this invention in an amount effective to treat the condition, disorder or disease of the subject being treated.

One of ordinary skill in the art will appreciate that pharmaceutically effective amounts of the AC5 inhibitor can be determined empirically and can be employed in pure form or, where such forms exist, in pharmaceutically acceptable salt, ester or prodrug form. The agents can be administered to a patient as pharmaceutical compositions in combination with one or more pharmaceutically acceptable excipients. It will be understood that, when administered to, for example, a human patient, the total daily usage of the agents or composition of the present invention will be decided within the scope of sound medical judgment by the attending physician. The specific therapeutically effective dose level for any particular patient will depend upon a variety of factors: the type and degree of the cellular response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

For example, satisfactory results are obtained by oral administration of the compounds at dosages on the order of from 0.05 to 500 mg/kg/day, preferably 0.1 to 100 mg/kg/day, more preferably 1 to 50 mg/kg/day, administered once or, in divided doses, 2 to 4 times per day. On administration parenterally, for example, by i.v. bolus, drip or infusion, dosages on the order of from 0.01 to 1000 mg/kg/day, preferably 0.05 to 500 mg/kg/day, and more preferably 0.1 to 100 mg/kg/day, can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging can also be arranged in a patient specific manner to provide a predetermined concentration of the agents in the blood, as determined by techniques accepted and routine in the art (HPLC is preferred). Thus patient dosaging can be adjusted to achieve regular on-going blood levels, as measured by HPLC, on the order of from 50 to 5000 ng/ml, preferably 100 to 2500 ng/ml.

In the adult, the doses are generally from about 0.001 to about 100, preferably about 0.001 to about 50, mg/kg body weight per day by inhalation, from about 0.01 to about 100, preferably 0.1 to 70, more especially 0.5 to 20, 30, 40, 50 or 60, mg/kg body weight per day by oral administration, and from about 0.001 to about 70, preferably 0.01 to 10, 20, 30, 40 or 50, mg/kg body weight per day by intravenous administration. In each particular case, the doses are determined in accordance with the factors distinctive to the patient to be treated, such as age, weight, general state of health and other characteristics, which can influence the efficacy of the compound according to the invention.

For example, when administered during or after reperfusion, the dose of AC5 inhibitor required to reduce damage to the myocardium and/or improve long term cardiac function may be less than doses previously administered to humans. In this embodiment, for patients suffering from an ischemic injury such as, but not limited to, myocardial infarction or Acute Coronary Syndrome, and requiring coronary artery reperfusion, it is expected that effective doses of the AC5 inhibitor Ara-Ade will be less that 1 mg/kg, less than 0.1 mg/kg, or about 0.06 mg/kg, than the antiviral doses of 10-30 mg/kg used in humans. In this embodiment, the compound can be administered as a single i.v. infusion.

The following non-limiting reaction schemes demonstrate how compounds according to the invention may be made.

The following non-limiting examples provide general chemical procedures for the synthesis of compounds according to the invention. While in no way intending to be bound by theory or limited, the following procedures refer to preparation of compounds according to Schemes I-X in order to more fully describe the invention.

EXAMPLES

Example 1

Generation of Knockout Mice

The targeting construct was prepared by ligating a 2.2-kb XhoI-PstI fragment from the 5' end of the type 5 AC gene, containing the exon with the first translation initiation site (5'-arm), a 1.7-kb fragment containing a neomycin resistance gene fragment (neo) driven by a phosphoglycerate kinase (PGK) promoter, and a BssHII-NcoI 7.0-kb fragment of the type 5 AC gene (3'-arm), into pBluscript II KS (Stratagene, La Jolla, Calif., USA). The type 5 AC gene has another translational start site accompanied by a reasonable Kozak consensus sequence located 738-bp downstream of the first translational start site within the same exon. To impair the second site, inventors excised a 0.15 kb PstI-BssHII fragment containing the second ATG and replaced it with a PGK-neo cassette in the final targeting vector as described in U.S. Ser. No. 10/429,214, the disclosure of which is incorporated herein by reference.

Embryonic stem cells were transfected with 50 μg linearized targeting vector by electroporation (Bio-Rad Gene pulsar set at 250 V and 960° F.). G418 (200 μg/ml) selection was applied 48 hours after transfection and resistant clones were isolated after 7-10 days of transfection. Subsequently, inventors obtained 576 clones. Genomic DNA from these resistant clones was digested with KpnI and probed with a 5' probe. Digesting genomic DNA with BamHI and probing with a 3' probe reconfirmed 8 positive clones. A single integration of the targeting vector was confirmed by a neo-probe. Two clones (clones #314 and #378) were injected into C57BL/6 blastocysts and chimeras were obtained. These chimeras successfully allowed germ-line transmission and were crossed with C57BL/6 females. F1-heterozygous offspring were then interbred to produce homozygous mutations. All mice were 129/SvJ-057BL/6 mixed background litter mates from F1 heterozygote crosses. All experiments were performed in 4-6 month old homozygous AC5KO and wild-type (WT) littermates.

Rotor Rod Test

The locomotor activity of intact animals, AC5KO versus WT was examined. At first glance the animals appeared normal, being neither catatonic nor rigid. However, standard behavior tests revealed that the mice had a significant impairment in motor function. The mice were studied using a rotor rod test in which mice were placed on a rotating rod and had to make continuous adjustment in balance in order to remain upright. The time that the mice spent on the accelerating rotor rod without falling was measured. The rod increased from 3 rpm to 30 rpm during each 5 min. trial. Each mouse went through 5 trials, which showed a gradual increase in the time on a rod showing "learning effects". There was no significant difference between WT and Hetero at the $1^{st}$ through $4^{th}$ trial. At the $5^{th}$ trial, there was a small but significant decrease in their performance in Hetero. AC5KO, by contrast, showed a significant improvement at the $1^{st}$ trial and constantly had and constantly has a shorter time on a rotor rod with poor learning effect, suggesting that the locomotor activity in AC5KO was significantly impaired.

RNase Protection Assay

Partial fragments of mouse AC cDNA clones for each isoform (types 1-9) were obtained by PCR. Sequencing and restriction mapping verified these cDNA fragments. Total RNA was isolated using RNeasy Midi kit (QIAGEN, Valencia, Calif., USA). Single strand cDNA was synthesized from total RNA using reverse transcriptase. The plasmid constructs were linearized by appropriate restriction enzyme. $^{32}$P-labeled cRNA probes were then generated using the Riboprobe Systems (Promega, Madison, Wis., USA). A human 28S ribosomal RNA probe was used as an internal control. RNase protection assay was performed using the RPA III kit (Ambion, Austin, Tex., USA) as suggested by the manufacture, followed by analysis on a 5% polyacrylamide-urea gel. Gels were exposed to X-OMAT film (Kodak, Rochester, N.Y., USA) for quantitation.

AC Assay and Tissue cAMP Measurement

Hearts were dissected from the mice and membrane preparations were prepared as described previously. Protein concentration was measured by the method of Bradford using bovine serum albumin as a standard. AC activity was measured as described previously. AC activity was linear within the incubation time up to 30 min. In order to harvest hearts for tissue cAMP content measurements, mice were allowed to acclimate to the surroundings in the laboratory for an hour before sacrifice. Freshly isolated hearts were briefly immersed in liquid nitrogen. The tissue was homogenized in ice-cold 6% percholic acid, and cAMP was extracted as described before. The concentration of cAMP was determined with an RIA kit (PerkinElmer Life Sciences, Boston, Mass., USA).

Physiological Studies

AC5KO (6.4+/−0.2 month old, n=6) and WT (6.7+/−0.1 month old, n=6) of either sex from the same genetic background as the transgenic mice were used for the physiological studies. Measurements of LV ejection fraction (LVEF) were performed as described previously. Briefly, after determination of body weight, mice were anesthetized with ketamine (0.065 mg/g), acepromazine (0.002 mg/g), and xylazine (0.013 mg/g) injected intraperitoneally and were allowed to breathe spontaneously. Echocardiography was performed using ultrasonography (Sequoia C256; Acuson Corporation, Mountain View, Calif., USA). A dynamically focused 15-MHz annular array transducer was applied from below, using a warmed saline bag as a standoff. M-mode echocardiographic measurements of the LV were performed at baseline and during intravenous infusion of ISO (0.005, 0.01, 0.02, and 0.04 µg/kg/min i.v. for 5 minutes each) (Abbott Laboratories Inc, North Chicago, Ill., USA) using an infusion pump (PHD 2000; Harvard Apparatus, Inc., Holliston, Mass., USA). The total amount of the infusion volume was <100 µL in each mouse. On a separate occasion, each mouse received an infusion of saline as a control to ensure that the volume of infusion alone did not contribute to enhance ventricular performance. To examine the responses to a muscarinic agonist, intraperitoneal (i.p.) infusion of Ach (25 mg/kg) was performed on top of the i.v. infusion of ISO (0.04 µg/kg/min).

In AC5KO and WT mice, four ECG wires (New England Electric Wire Corporation, Lisbon, N.H., USA) were placed subcutaneously, a silicone elastomer tubing (Cardiovascular Instrument Corp., Wakefield, Mass., USA) was inserted into the right external jugular vein and a 1.4 F micromanometer catheter (Millar Instruments, Inc., Houston, Tex., USA) was inserted into the lower abdominal aorta via the femoral artery as described previously with some modifications. The ECG wires, the silicone elastomer tubing and the micromanometer catheter were tunneled subcutaneously to the back, externalized, and secured in a plastic cap. On the day of the study, each mouse was placed in the mouse holder, the jugular venous catheter was accessed and connected to a microliter syringe (Hamilton Co., Reno, Nev., USA), the 1.4 F micromanometer catheter was connected to a recorder (Dash 4u; Astro-Med, Inc., West Warwick, R.I., USA) and the ECG wires were connected to an ECG amplifier (Gould Inc., Cleveland, Ohio, USA). All experiments were recorded with animals in the conscious state. After at least 6 hours recovery from the implantation of the catheter, when a stable heart rate (HR) was achieved, the baseline ECG and arterial pressure (AP) were recorded for 5 min. Ach (0.05 µg/g) was then administered intravenously (i.v.), and the ECG and AP recording were repeated. A recovery period of 15 min was allowed for the HR and AP to return to baseline before administering the next drug. Baseline HR slowing was examined in response to phenylephrine (0.2 µg i.v.).

Statistics

All data are reported as mean+/−SEM. Comparisons between AC5KO and WT values were made using a t-test. PG0.05 was taken as a minimal level of significance.

Results:

Targeted Disruption of the Type 5 AC Gene.

The type 5 AC gene was disrupted in mice using homologous recombination as described in U.S. Ser. No. 10/429,214, the disclosure of which is incorporated herein by reference. Mice were genotyped by Southern blotting using genomic DNA from tail biopsies. mRNA expression of the type 5 AC in heterozygous mice was approximately half of that in WT and it was undetectable in AC5KO. The growth, general appearance and behavior were similar to those of WT.

No Compensatory Increase in the Other Isoforms of AC.

Whether there were compensatory increases in the expression of the other isoforms of AC in AC5KO was investigated. Since AC isoform antibodies that can convincingly determine the level of protein expression of all the isoforms are not available, inventors quantitated the mRNA expression of the AC isoforms by an RNase protection assay. cRNA of the 28S ribosomal RNA was used as an internal control. Types 3, 4, 6, 7 and 9 AC were readily detected, but not increased, while types 1, 2, and 8 were hardly detectable, arguing that type 6 AC, a homologue of type 5 AC in the heart, could not compensate for the type 5 AC deficiency. AC activity was decreased in the hearts of AC5KO in vitro.

cAMP production in membranes from the hearts of AC5KO and WT at 6 months of age was examined. The steady state AC activity was determined as the maximal capacity of cAMP production in the presence of ISO (100 µM ISO+100 µM GTP), GTPγS (100 µM) or forskolin (100 µM). AC activity was decreased in AC5KO relative to that in WT by 35+/−4.3% (basal), 27+/−4.6% (ISO), 27+/−2.4% (GTPγS), and 40+/−4.7% (forskolin). These data indicate that type 5 AC, as the major isoform in the heart, is responsible for approximately 30-40% of total AC activity in the mouse heart. However, cardiac tissue cAMP content was not significantly decreased in AC5KO compared to WT (55+/−7.5 vs 62+/−3.4 pmol/mg protein, respectively, n=4, p=NS). Carbachol (10 µM), a muscarinic agonist, decreased ISO-stimulated AC activity by 21+/−3.4% in WT, but did not inhibit ISO-stimulated AC activity in AC5KO. Basal cardiac function was not decreased, but the response to ISO and muscarinic inhibition of ISO were attenuated.

The cardiac responses to i.v. ISO on LVEF and fractional shortening (FS) in AC5KO were attenuated as expected (data not shown, Okumura et al. Circulation. 116(16):1776-1783). However, baseline cardiac function tended to be increased; LVEF (WT vs. AC5KO; 59+/−2.4% vs. 64+/−4.3%) and FS (26+/−1.4% vs. 29+/−2.7%). Muscarinic inhibition of ISO stimulated cardiac function, as measured by LVEF, was prominent in WT, as expected, but was abolished in AC5KO.

Parasympathetic (Muscarinic) Control of HR.

In the presence of ISO, Ach reduced HR in WT, but not in AC5KO. Baseline HR was significantly elevated in conscious AC5KO. Muscarinic stimulation in conscious WT with Ach (0.01 µg/g i.v.) decreased HR by 22% but significantly less (7.5%) in AC5KO. Phenylephrine (0.2 µg/g i.v.) increased systolic arterial pressure significantly in both WT and AC5KO, but induced less baroreflex mediated slowing of HR in AC5KO than in WT. The increase in HR following atropine (1 µg/g i.v.), in WT (102+/−22.2 beats/min) was not observed in AC5KO (19+/−7.5 beats/min).

AC is critical to regulating cardiac contractility and rate, particularly in response to sympathetic activation. The rate of cardiac contraction is also under sympathetic control, but parasympathetic mechanisms may be even more important in its regulation, particularly with regard to reflex cardiac slowing. Importantly, AC is involved in parasympathetic modulation of cardiac function and HR, particularly in the presence of sympathetic stimulation.

A key mechanistic approach to understanding the role of AC in vivo is to alter AC genetically in the heart. Previous studies have overexpressed types 5, 6 and 8 AC in the heart. These studies found the expected increases in response to β-AR stimulation, but failed to observe any changes in parasympathetic control. Although targeted disruption of cardiac AC would be the preferred experimental approach to understand the mechanistic role of AC in the heart, this has not been accomplished previously. More importantly, there is not one AC, but rather 9 mammalian membrane-bound AC isoforms and significant heterogeneity exists in their distribution and biochemical properties, such that function of the isoforms may differ even within the same tissue. One laboratory deleted types 1, 3 and 8 AC, but the effects on cardiac function were not delineated. Inventors selected type 5 AC for deletion in this investigation, since this is the major AC isoform in the adult heart, which was confirmed in cardiac membrane preparations from AC5KO, where 30-40% of AC activity was lost. In addition, its biochemical properties reflect the overall signature of cardiac AC, in that types 5 and 6 are sensitive to direct inhibition by Gi.

The AC5KO mouse provides an excellent model to study AC isoform specific regulation of the heart. The in vitro experiments confirmed that type 5 AC is the major isoform in the heart, and that in vivo, ISO stimulation of cardiac function and rate were blunted. Since type 5 AC is the major AC isoform expressed in the adult mouse heart, it was surprising to find no effect on baseline cardiac function, but rather an increase in HR, despite reduced baseline AC activity. Paradoxically, the increased basal HR, is more likely related to a loss of parasympathetic restraint, since loss of sympathetic stimulation would act in the opposite direction. The blunted parasympathetic restraint was also observed in response to baroreflex mediated bradycardia, and conversely, atropine induced less tachycardia in the AC5KO than in the WT. Thus, type 5 AC regulates cardiac inotropy and chronotropy through both the sympathetic and parasympathetic arms of the autonomic nervous system.

Example 2

AC Assay

Hearts were dissected from the mice, and membrane preparations were prepared. Protein concentration was measured by the Bradford method using bovine serum albumin as a standard. AC activity was measured as described previously. AC activity was linear within the incubation time up to 30 min. For the study of $Ca^{2+}$ inhibition, the membranes were treated first with EGTA to extract the endogenous $Ca^{2+}$ prior to the assay. Free $Ca^{2+}$ concentrations were obtained with the use of 200 µmol/L EGTA buffers as described previously. The experiments with $Ca^{2+}$ inhibition were conducted in the presence of 100 µmol/L isoproterenol (ISO) plus 100 µmol/L GTP.

Physiological Studies

Electrocardiogram (ECG) wires, a jugular vein catheter for drug infusion, and a femoral artery catheter for arterial pressure monitoring were implanted under anesthesia. Measurements of left ventricular ejection fraction (LVEF) were taken using echocardiography under anesthesia with 2.5% tribromomethanol (0.010-0.015 ml/g body wt) injected intraperitoneally (i.p.). Intravenous (i.v.) infusion of ISO (0.04 µg/kg/min i.v. for 5 min) was performed using an infusion pump. To examine the responses to a muscarinic agonist, acetylcholine (ACh) (25 mg/kg i.p.) was co-administered i.p. during the i.v. infusion of ISO (0.04 µg/kg/min). In addition, in conscious mice ACh (0.01 and 0.05 mg/kg), atropine (0.25, 1 and 2 mg/kg), or verapamil (0.75 mg/kg) were administered i.v., and the ECG was recorded. A recovery period of 15 min was allowed for the HR to return to baseline before administering the next drug. To examine HR responses to baroreflex hypertension, phenylephrine (0.2 mg/kg i.v.) was infused, and the ECG and arterial pressure were measured.

Pathology

The pathological examination included assessment of body weight, heart weight, and light microscopy of hematoxylin- and eosin-stained sections of the left ventricle.

Radioligand Binding Assays and Western Blotting

Radioligand binding assays for α-AR were conducted using the above membrane preparations and $^{125}$I-cyanopindolol. Western blotting for Gsα, Giα, Gqα, Gβa, α1-adrenergic receptor (α1-AR), α-adrenergic receptor kinase (α-ARK) and muscarinic receptor type 2 were conducted using either the membrane preparation or whole tissue homogenates.

Electrophysiological Studies

Whole-cell currents were recorded using patch-clamp techniques. Cell capacitance was measured using voltage ramps of 0.8 V/s from a holding potential of −50 mV. All experiments were performed at room temperature. $Ca^{2+}$ channel currents (ICa) were measured with an external solution (mmol/L): $CaCl_2$ or $BaCl_2$; $MgCl_2$; tetraethyl ammonium chloride 135; 4-aminopyridine 5; glucose 10; and HEPES, 10 (pH 7.3). The pipette solution contained (mmol/L): Cs-aspartate, 100; CsCl, 20; $MgCl_2$, 1; MgATP, 2; GTP, 0.5; EGTA, 5 or 1,2-bis(2-aminophenoxy)ethane-N,N,N',N'-tetraacetic acid (BAPTA), 10 and HEPES, 5 (pH 7.3). For potassium ($K^+$) channel current recordings, the external solution was normal Tyrode's solution (mmol/L): NaCl, 135; $CaCl_2$, 1.8; $MgCl_2$, 1; KCl, 5.4; glucose, 10; HEPES, 10 (pH 7.3). Nifedipine (10 μmol/L) was added to block L-type $Ca^{2+}$ channel currents. The patch pipette solution contained (mmol/L): potassium aspartate, 110; KCl, 20; $MgCl_2$, 2; ATP, 2; GTP, 0.5; EGTA, 5; HEPES, 5 (pH 7.3).

Statistical Analysis

All data are reported as mean+/−SEM. Comparisons between AC5−/− and WT values were made using a Student's t-test. For statistical analysis of data from multiple groups, one way ANOVA was used, with Bonferroni post hoc test. P<0.05 was taken as a minimal level of significance.

Results:

AC Activity was Decreased in the Heart of AC5KO in Vitro cAMP production in membranes from the hearts of AC5KO and WT mice at the age of 6 months were examined. The steady state AC activity in the membrane preparation was determined as the maximal capacity of cAMP production in the presence of ISO (100 won, ISO+100 μmol/L GTP), guanosine-5'-O-(3-triophosphate) GTPαS (100 μmol/L), or forskolin (100 μmol/L). AC activity was decreased in AC5KO relative to that of WT by 35+/−4% (basal), 27+/−5% (ISO), 27+/−2% (GTPγS), and 40+/−5% (forskolin). More specifically, ISO increased AC activity by 78+/−6 pmol/15 min/mg in WT, but only 64+/−4 pmol/15 min/mg in AC5KO, indicating that the response to ISO was attenuated in AC5KO. These data indicate that type 5AC is responsible for approximately 30%-40% of the total AC activity in the mouse heart Carbachol (10 μmol/L), a muscarinic agonist, decreased ISO stimulated activity by 21+/−3% in WT, but this was hardly detectable in AC5KO, indicating that muscarinic (Gi induced) inhibition of the AC activity is markedly attenuated in AC5KO.

Regulation of AC Activity by Free $Ca^{2+}$

To investigate the modulation of AC activity by free $Ca^{2+}$, cAMP production was examined in membranes from the hearts of WT and AC5KO at different $Ca^{2+}$ concentrations in the presence of ISO (100 μmol/L ISO+100 μmol/L GTP). The ISO-stimulated AC activity was inhibited by increasing concentrations of $Ca^{2+}$ as expected in WT. The $Ca^{2+}$ inhibition of AC activity was impaired in AC5KO. The reduction in magnitude of inhibition was most apparent in AC5KO, i.e., in the submicromolar range of $Ca^{2+}$.

Basal Cardiac Function was not Decreased, but the Response to ISO and Muscarinic Inhibition of ISO were Impaired The cardiac responses to i.v. ISO on LVEF in AC5KO were attenuated as expected. However, baseline cardiac function was not different between WT and AC5KO; LVEF (WT vs. AC5KO: 70+/−1.2% vs. 70+/−1.5%, n=10-11); fractional shortening (WT vs. AC5KO: 33+/−0.9% vs. 33+/−1.0%, n=10-11). Muscarinic inhibition of ISO stimulated cardiac function, as measured by LVEF, was prominent in WT, as expected, but was attenuated in AC5KO, suggesting that muscarinic inhibition of α-adrenergic stimulation was impaired.

| | WT(n) | AC5KO |
|---|---|---|
| Age(month) | 4.4+/−0.1(15) | 4.2+/−0.2(15) |
| BW(g) | 25+/−1.0(15) | 27+/−1.0(14) |
| LV/BW(mg/g) | 3.9+/−0.1 (9) | 4.1+/−0.2(8) |
| HR(bpm) | 523+/−11(15) | 613+/−8(14) |
| *LVDD(mm) | 3.9+/−0.1(11) | 4.0+/−0.1(10) |
| LVSD(mm) | 2.6+/−0.09(11) | 2.7+/−0.1(10) |
| LVEF(%) | 70+/−1.2(11) | 70+/−1.5(10) |
| % FS | 33+/−0.9(11) | 33+/−1.0(10) |

Data are mean+/−SEM HR is under conscious state and other functional data are under anesthesia LVEF: Left Ventricular Ejection Fraction LVDD: LV end-diastolic diameter LVSD: LV end-systolic diameter % FS: % fractional shortening *P<0.01

Parasympathetic (Muscarinic) Control of HR

Baseline HR was significantly elevated in conscious AC5KO (WT vs. AC5KO: 523+/−11 vs. 613+/−8 beats/min, P<0.01, n=14-15). The increase in HR following muscarinic receptor blockade by atropine (1 mg/kg i.v.) in WT was not observed in AC5KO. Muscarinic stimulation in conscious WT with ACh (0.01 mg/kg i.v.) decreased HR by 15% but significantly less (1.3%) in AC5KO. However, high doses of ACh (0.05 mg/kg i.v.) decreased HR similarly in both WT and AC5KO. At the higher doses of ACh, it is possible that the lack of AC5 inhibition was overwhelmed. In contrast, verapamil, which decreases HR through a non-muscarinic mechanism, reduced HR in AC5KO and WT similarly (−33+/−10 vs. −36+/−10 beats/min). These findings suggest that muscarinic inhibition was impaired in the conscious state in the absence of ISO-stimulation in AC5KO. To confirm that muscarinic, and therefore parasympathetic, neural regulation of the heart was changed, phenylephrine (0.2 mg/kg i.v.) was injected to elevate arterial pressure transiently through vasoconstriction and to induce baroreflex-mediated slowing of HR. Phenylephrine increased systolic arterial pressure similarly in both WT and AC5KO. However, the degree of HR slowing was significantly less in AC5KO than in WT, suggesting that the baroreflex, most likely through its parasympathetic control, was attenuated in AC5KO.

$K^+$ Current Activity

Normal pacemaker activity is also regulated by vagal stimulation via muscarinic receptor-coupled $K^+$ channels, i.e., GIRK (G-protein-activated inwardly rectifying $K^+$ channel), independent of intermediary signaling. To determine whether enhanced baseline HR and blunted response to muscarinic agonists in AC5KO are due to changes in the $K^+$ channel, muscarinic receptor coupled $K^+$ channel currents were examined in atrial myocytes. Rapid application of carbachol elicited an outward $K^+$ current via Gi proteins. The carbachol-induced currents rose quickly to a peak and then decayed slowly to a steady level. The peak amplitude and decay time were similar between WT and AC5KO myocytes. These results indicate that coupling between muscarinic receptors and the Gi-gated $K^+$ channel are not altered in AC5KO myocytes.

Using a mouse model with disruption of the major AC isoform (AC5KO), it was predictable that increases in cardiac function in response to ISO would be diminished in AC5KO, as was demonstrated. Indeed the decrease in cardiac responsiveness to ISO in vivo paralleled the data in vitro on AC activity. Since overexpression of type 5 AC in the heart enhanced cardiac function, it had been expected that baseline cardiac function and HR would be reduced in AC5KO, which was not observed. Despite the decrease in AC activity, basal cardiac function and HR were not decreased in AC5KO. Actually, HR was significantly elevated in conscious AC5KO. At least three mechanisms are impaired in AC5KO: 1) muscarinic inhibition of AC activity, 2) baroreflex restraint of HR, and 3) $Ca^{2+}$ mediated inhibition of AC activity. Since the elevated HR was not likely due to enhanced sympathetic tone, i.e., sympathetic responses were attenuated in AC5KO in both in vivo and in vitro experiments. This may be due, at least in part, to the loss of parasympathetic inhibition, since type 5 AC is a major Gi-inhibitable isoform in the adult heart. It was demonstrated that muscarinic stimulation, which inhibits cardiac function and HR, was attenuated in AC5KO both in the presence and absence of enhanced β-AR stimulation with ISO. Conversely, atropine increased HR in WT, but not in AC5KO, supporting the concept that the higher baseline HR was due to the loss of parasympathetic restraint. Furthermore, the arterial baroreflex slowing of HR, which occurs through parasympathetic nerves, was also blunted in the AC5KO. Therefore, at any given arterial pressure there is less baroreflex restraint, resulting in elevated HR. These data provide convincing evidence in vivo that type 5 AC exerts a major role in parasympathetic regulation of cardiac function in addition to its key role in sympathetic regulation. Thus, AC-mediated parasympathetic modulation of ventricular function and atrial function, i.e., HR, must be considered along with the more widely recognized mechanisms involving muscarinic modulation of $K^+$ channel activity and muscarinic regulation at the level of membrane receptors, or Gi. To support this conclusion, the $K^+$ current in atrial myocytes and the expression of G proteins, β-ARK, muscarinic receptor type 2, and β- and a 1-AR were not altered in AC5KO. Also, the impaired $Ca^{2+}$ inhibition of AC may also contribute to the increased HR at baseline. These results lead to the conclusion that cardiac rate of contractility is also regulated at the level of AC.

Example 3

Adenine or its Analogs Inhibit AC5

As described previously in U.S. Ser. No. 10/429,214, the disclosure of which is incorporated herein by reference; "HI30435" showed a high selectivity to inhibit AC5. The result from a dose-response analysis and the determination of the $IC_{50}$ values are discussed below.

Selectivity among the AC isoforms was determined. The relative potency of HI30435, in comparison to classic AC inhibitor (3'-AMP) is shown as an example. HI30435 potently inhibited AC5 while that inhibited AC2 and AC3 only to a modest degree. The $IC_{50}$ values were calculated to be 0.32 μM for AC5, 11.1 μM for AC3, 65.3 μM for AC2. The selectivity ratio of HI30435 was 207 between AC5 and AC2. 3'-AMP showed a weak selectivity for AC5 in inhibiting AC catalytic activity. The $IC_{50}$ values were calculated to be 14.6 μM for AC5, 30.2 μM for AC3, 263 μM for AC2. The selectivity ratio was 18 between AC5 and AC2. These data suggest that HI30435 is extremely specific and strong inhibitor for AC5. Most importantly, HI30435, but not NKY80, inhibited cAMP accumulation in intact H9C2 cells. This suggests that membrane penetration of these compounds is important for biological activity and that HI30435, but not NKY80, has such a capability.

Example 4

Disruption of Type 5 AC Gene Preserves Cardiac Function Against Pressure Overload Chronic pressure overload is a cause of heart failure. In response to pressure overload, the myocardium undergoes adaptive hypertrophy in order to maintain cardiac output against the increased afterload. Prolonged pressure overload eventually leads to heart failure as reflected by the dilatation of the Left Ventricle (LV) and a decrease in cardiac contractility, e.g. Left Ventricular Ejection Fraction (LVEF). Pressure overload also results in apoptosis, which is thought to be part of the mechanism of cardiac decompensation. The role of the beta adrenergic (β-AR) signaling is well defined as a primary defense against acute stress or changes in hemodynamic load; however, uncertainty remains about its role in the pathogenesis of heart failure. The purpose of the experiment below was to examine the effects of chronic pressure overload induced by aortic banding in AC5KO and Wild Type (WT) controls. Specifically, the extent to which LV hypertrophy and apoptosis developed in response to pressure overload and the resultant effects on cardiac function were examined.

Aortic Banding

Transverse aortic banding or sham operation was performed in 4-6 month-old homozygous AC5KO and WT littermates. The method of imposing pressure overload in mice has been described previously. Mice were anesthetized intraperitoneally with a mixture of ketamine (0.065 mg/g), xylazine (0.013 mg/g), and acepromazine (0.002 mg/g). Mice were ventilated via intubation with a tidal volume of 0.2 ml and a respiratory rate of 110 breaths per minute. The left side of the chest was opened at the second intercostal space and the transverse thoracic aorta was constricted. To measure the pressure gradient across the constriction, two high-fidelity catheter tip transducers (1.4F; Millar Instruments Inc.) were used at one week after aortic banding. One was inserted into the right carotid artery and the other into the right femoral artery, and they were advanced carefully to the ascending aorta and abdominal aorta, respectively, where pressures were measured simultaneously.

Echocardiography

Mice were anesthetized as already discussed. Echocardiography was performed using ultrasonography (Sequoia C256; Acuson Corporation). A dynamically focused 13 MHz annular array transducer was applied from below, using a warmed saline bag as a standoff. M-mode measurements of LV internal diameter were made from more than three beats and averaged. Measurements of the LV end-diastolic diameter (LVEDD) were taken at the time of the apparent maximal LV diastolic dimension, while measurements of the LV end-systolic diameter (LVESD) were taken at the time of the most anterior systolic excursion of the posterior wall. LVEF was calculated by the cubic method: LVEF (%)=[(LVEDD)$^3$−(LVESD)$^3$]/(LVEDD)$^3$.

Evaluation of Apoptosis

DNA fragmentation was detected in situ by using TUNEL staining. Briefly, deparaffinized sections were incubated with proteinase K and DNA fragments labeled with biotin-conjugated dUTP and terminal deoxyribonucleotide transferase and visualized with FITC-ExtrAvidin (Sigma-Aldrich). Nuclear density was determined by manual counting of 4',6-diamidine-2'-phenylindole dihydrochloride (DAPI)-stained nuclei in six fields of each animal using the 40× objective, and the number of TUNEL-positive nuclei was counted by examining the entire section using the same power objective. Limiting the counting of total nuclei and TUNEL-positive nuclei to areas with a true cross section of myocytes made it possible to selectively count only those nuclei that were clearly within myocytes. For some samples, triple staining with propidium iodide (Vector Laboratories Inc.), TUNEL, and anti-α-sarcomeric actin antibody (Sigma-Aldrich), and subsequent analyses using confocal microscopy, were performed in order to verify the results obtained with light microscopy.

Myocyte Cross-Sectional Area

Myocyte cross-sectional area was measured from images captured from silver-stained 1-μm-thick methacrylate sections. Suitable cross sections were defined as having nearly circular capillary profiles and circular-to-oval myocyte sections. No correction for oblique sectioning was made. The outline of 100-200 myocytes was traced in each section. MetaMorph image system software (Universal Imaging Corp.) was used to determine myocyte cross-sectional area.

Western Blotting

Crude cardiac membrane fractions were prepared and separated on 4-20% SDS-polyacrylamide gel and blotted onto nitrocellulose membrane. Western blotting was conducted with anti-Bcl-2 and anti-Bax antibodies (BD Biosciences). Expression of these proteins was quantified by densitometry.

RNase Protection Assay

Total mRNA in the heart was prepared, and the amount of mRNA of Bcl-2 was determined by RNase protection assay using RPA III kit (Ambion). To probe Bcl-2, a partial fragment of mouse Bcl-2 gene was obtained by RT-PCR. A human 18S rRNA probe was used as an internal control. The relative intensity of Bcl-2 to 18S rRNA was quantified by densitometry.

Statistical Analysis

All data are reported as mean+/−SEM. Comparisons between AC5KO and WT values were made using Student's t-test. For statistical analysis of data from multiple groups, ANOVA was used. P<0.05 was taken as a minimal level of significance.

Results:

Disruption of Type 5 AC Did Not Affect the Development of Cardiac Hypertrophy

At baseline, there was no difference between WT and AC5KO in the LV weight (LVW; mg)/tibial length (TL; mm) (WT 4:7+/−0.2, AC5KO 5:1+/−0.2 mg/mm, n=9-14, P=NS). The time course and the degree of the development of cardiac hypertrophy (LVW/TL) in response to pressure overload were similar between WT and AC5KO. LVW/body weight, another index of cardiac hypertrophy, confirmed the data from LVW/TL. Myocyte cross-sectional area, another index of hypertrophy, increased similarly in both WT and AC5KO at 3 weeks of banding, confirming the gross pathological data.

Cardiac Function was Preserved in AC5KO after 3 Weeks of Aortic Banding

LV dimensions and cardiac function were evaluated echocardiographically. There was no difference in LVEDD and LVEF between WT and AC5KO at baseline and a 1 week after banding when they were compared to each other or to sham-operated animals. At 3 weeks after banding, however, LVEDD was significantly increased in WT, while it remained unchanged in AC5KO. Similarly, LVEF fell significantly from 70+/−2.8 to 57+/−3.9% (P<0.05, n=8-11) in WT, while it remained unchanged at 74+/−2.2% in AC5KO. These results suggest that cardiac function was protected following chronic pressure overload in AC5KO. This was not due to a difference in pressure gradient, which was similar at 1 week after banding in AC5KO (102+/−8.2 mmHg) vs. WT (112+/−3.1 mmHg). Heart rate was not significantly different in WT and AC5KO under anesthesia during echocardiography, but was elevated in the conscious state in AC5KO.

Apoptosis was Protected in AC5KO at 1 Week of Banding.

Before banding, there was no difference in the number of TUNEL-positive cells between the two groups, suggesting that the lack of type 5 AC did not alter the viability of cardiac myocytes at baseline. Aortic banding increased the number of TUNEL-positive cells in WT roughly 4-fold, at both 1 and 3 weeks after aortic banding. The increase in apoptosis was roughly half that of WT at 3 weeks and less at 1 week after banding.

Expression of Bcl-2 is Enhanced in AC5KO Hearts in Response to Pressure Overload To examine changes in the molecules that are involved in apoptosis signaling, Bcl-2, an inhibitor of apoptosis, and Bax, an accelerator of apoptosis, were quantified in WT and AC5KO. Bcl-2 expression was hardly detectable in the sham groups. Interestingly, Bcl-2 protein expression was upregulated after 3 weeks of banding in both WT and AC5KO, although the magnitude of the increment was greater, P<0.05, in AC5KO. On the other hand, Bax expression was not different in the sham and banded groups. mRNA expression of Bcl-2 was also examined. In parallel with Bcl-2 protein, mRNA of Bcl-2 was upregulated after 3 weeks of banding in both WT and AC5KO, but the magnitude of the increment was not different between WT and AC5KO. These results suggest that the apoptotic process is attenuated, at least in part, through the post-transcriptional regulation of Bcl-2 in AC5KO hearts.

Example 5

Materials and Methods

Tenofovir diphosphate (PMPA-PP), zidovudine monophosphate (MP), zidovudine diphosphate (PP), zidovudine triphosphate (TP), famciclovir penciclovir and valaciclovir were purchased from Moravek. Formycin A (FMA) and Formycin B (FMB) were purchased from Berry and Associates. All other reagents were from Sigma unless specified. Long-term infusion of isoproterenol (Sigma, St. Louis, Mo.) was performed for 7 days at a dose of 60 mg/kg/d with or without AC5 inhibitors by using a miniosmotic pump (ALZET model 2001, DURECT Corp, Cupertino, Calif.). Control mice received vehicle in pumps. Pumps were removed 24 hours before biochemical and physiological studies. Experiments were performed in 3- to 5-month-old male C57Bl/6, and in AC5Tg transgenic mice. This study was approved by the Animal Care and Use Committee at New Jersey Medical School.

Mice were anesthetized with 2.5% tribromoethanol (0.010 to 0.015 mL per gram of body weight) injected intraperitoneally, and echocardiography was performed with ultrasonography (ACUSON *Sequoia* C256, Siemens Medical Solutions, Malvern, Pa.). For acute injection of isoproterenol, forskolin and milrinon, a PE-10 catheter was inserted into the right jugular vein, and drugs were injected at the rate of 1 μl/s. cAMP accumulation assay in H9C2 cells, a cardiac myoblast cell line, was examined as previously described.

Hearts and striatum were dissected from the mice and membrane preparations were made as previously described. This crude membrane preparation was used in the AC assay. AC activity was measured by a modification of the method of Salomon et al. as previously described. When AC assay was performed using crude membranes from AC6Tg mice heart, manganese was used instead of magnesium in the assay buffer because AC6 is more stimulated by magnesium than by manganese. Double-reciprocal plots were examined as previously described.

Western blotting was conducted with commercially available antibodies, except for type 5 and type 6 AC. Western blotting for type 5 and 6 AC was performed as previously described. Protein expression was quantified by densitometry.

Four days after the implantation, Rotarod performance test and pole test were examined as previously described. For MPTP injection (1-methyl 4-phenyl 1,2,3,6-tetrahydropyridine), mice were injected intraperitoneally (i.p.) with 0.1 mL of PBS or MPTP dissolved in PBS at 24-hour intervals for 5 days. The daily dose of MPTP was 30 mg/kg. Ara-Ade (9-13-D-ribofuranosyladenine) was delivered by the use of the mini osmotic pump as described above.

Treadmill exercise tolerance was performed as previously described. One week after pump implantation, pumps were removed under anesthesia. The next day after removal, mice were placed on a custom-built four-lane treadmill with an infrared detection system above the shock stimulus at a starting speed of 2 m/min. Every two minutes, the speed was increased by 4 m/min for 16 min or until the mouse could no longer run.

Statistical comparisons among analyses was calculated using Student's t-test or ANOVA with Bonferroni post hoc test. P values of <0.05 will be considered significant. Data are means.+−.SEM unless specified.

Ara-Ade is a Specific AC5 Inhibitor.

Various compounds with adenine-like backbone structure were screened because this structure is essential for both AC inhibition and plasma membrane permeability. Drug effects on AC activity was examined by using membrane preparations from mouse heart and striatum, in which AC5 provides 20% and 80% of total AC activity, respectively. Several compounds have AC5 inhibitory activity. Among them, Ara-Ade, fludarabine, FMA, PMPA-PP, 2-fluoroadenosine, 2-fluoro-2'-deoxyadenosine and zidovudine-TP showed more than 50% of inhibition in the striatum membrane (Table 1). Unlike these compounds, 3-deazaadenosine showed greater in the heart membrane than the striatum membrane, i.e., the ratio of inhibition between the heart membrane and the stratum membrane was less than one, suggesting that 3-deazaadenosine has selectivity for another AC subtype(s) which dominantly expresses in the heart.

2'5' ddAdo showed greatest inhibition in cAMP accumulation as previously reported. FMA, fludarabine and 2-fluoroadenosine moderately inhibited cAMP accumulation, whereas Ara-Ade and cladribine showed slight inhibition. In contrast, AZT-TP, 3-deazaadenosine and PMPA-PP showed little inhibition in H9C2 cells, indicating that these compounds fail to cross the plasma membrane. Because of the adenine-like structure these compounds may compete with ATP for binding to ATP-binding molecules. This may cause a critical adverse effect. Whether these compounds are competitive with respect to ATP was examined. Ara-Ade, 2-fluoroadenosine and 2'5' ddAdo were non-competitive with respect to ATP while zidobudine-TP was competitive, suggesting that zidobudine-TP side effects arise from non-specific binding to ATP-binding molecules. Ara-Ade (9-β-D-ribofuranosyladenine) Inhibits AC5 in Vivo.

The effect of Ara-Ade on βAR-induced LVEF increase was examined. When Ara-Ade was chronically infused (20 mg/kg/day), LVEF was similar to vehicle at baseline, but lower after 0.25 μg/kg IV of ISO. In AC5Tg, the difference between vehicle and Ara-Ade was significant even at 0.05 μg/kg IV. This is in contrast to WT where there was no significant difference between vehicle and Ara-Ade. Thus, Ara-Ade selectively inhibits AC5 in vivo. The effect of chronic infusion of Ara-Ade on LVEF elevation in the presence of milrinone, a PDE3 inhibitor was examined. Milrinone infusion increased LVEF in both vehicle and Ara-Ade group with no significant difference, indicating that Ara-Ade exerts its effect only when βAR is stimulated, but not when PDE3 is inhibited. To further examine the selectivity of Ara-Ade for AC5, changes in HR in response to cholinergic receptor stimulation, which was reported to be attenuated in AC5KO, were examined. When carbachol, a cholinergic receptor agonist, was administered the decrease in HR was greater in vehicle than Ara-Ade, indicating that the effect of Ara-Ade on cholinergic receptor stimulation was similar to that in AC5KO. These data demonstrate that Ara-Ade selectively inhibits AC5 in vivo.

Ara-Ade Attenuates Contractile Dysfunction in Response to Chronic Catecholamine Stress.

Chronic ISO infusion with Ara-Ade and 2'5' ddAdo, another AC5 inhibitor, and metoprolol, a βAR blocker as a positive control were examined. When basal cardiac function was examined after 3-day drug administration, AC5 inhibitors did not change basal LVEF while metoprolol decreased it. HR changes under chronic ISO infusion with or without drugs were examined. There was no significant difference between groups, indicating that AC5 inhibitors are unlikely to cause bradycardia.

These drugs were examined on chronic ISO infusion. Chronic ISO infusion significantly decreased LVEF and FS; however, co-administration of 20 and 100 mg/kg/day of Ara-Ade or 20 mg/kg/day of 2'5' ddAdo rescued LVEF and FS reduction, indicating that AC5 inhibitors prevent ISO-induced contractile dysfunction. Metoprolol also rescued ISO-induced LVEF decrease. By contrast, neither Ara-Ade nor 2'5' ddAdo inhibited ISO-induced wall thickening such as changes in DESP or DPW, indicating that AC5 inhibitors play a minimal role in inhibiting cardiac hypertrophy. Moreover, the metoprolol treated group did not show significant increase in DESP and DPW, indicating that antagonizing βAR inhibits cardiac hypertrophy. The Ara-Ade- or 2'5' ddAdo-treated group showed increased LVW/BW and myocyte cross sectional area while metoprolol did not. For HR, only the ISO-treated group showed statistically significant decreased HR, indicating that both AC5 inhibitors and metoprolol rescue decreased HR by chronic ISO. To confirm the effect of AC5 inhibitors on cardiac function, the effect of Ara-Ade on exercise tolerance as a non-invasive cardiac function test was examined. AC5 inhibitors rescued ISO-induced decrease in the maximum velocity in the treadmill test demonstrating that Ara-Ade attenuates contractile dysfunction in response to chronic ISO.

Survival rate in chronic ISO with Ara-Ade or vehicle was calculated. Survival rate during 1-week was higher in the Ara-Ade group than in the vehicle group, strongly suggesting that Ara-Ade attenuates the progression of heart failure induced by catecholamine stress.

Ara-Ade Inhibits Cardiac Myocyte Apoptosis Via ERK/MEK/Bcl-2.

AC5KO showed decreased cardiac myocyte apoptosis after chronic ISO. The effect of AC5 inhibitors and metoprolol on changes in cardiac myocyte apoptosis was examined. All drugs significantly decreased ISO-induced myocardial apoptosis demonstrating that they rescue contractile function by inhibiting cardiac myocyte apoptosis. Since cardiac fibrosis is the result of replacement after myocardial apoptosis. Fibrosis was examined, and all drugs significantly decreased fibrosis area.

Molecular changes in the apoptosis signaling were examined. Ara-Ade significantly increased phosphorylation of Bcl-2, a major anti-apoptotic molecule. Ara-Ade activates the ERK/MEK signaling pathway, which is known to phosphorylate and activate Bcl-2. Ara-Ade increased phosphorylation of ERK1/2 and MEK, suggesting that Ara-Ade inhibits cardiac myocyte apoptosis via the ERK/MEK/Bcl-2 pathway.

Ara-Ade Did not Cause Motor Dysfunction.

The effect of Ara-Ade on motor function in mice was examined by the Rotarod test and the pole test. When MPTP, known to impair locomotor activity, was injected, the activities of the Rotarod and the pole test were significantly impaired. In contrast, Ara-Ade did not change these performances, indicating that, when administered, Ara-Ade is unlikely to impair motor function.

Example 6

AC5KO mice will be generated as previously described. Ara-Ade will be delivered with a mini-osmotic pump implanted subcutaneously. Three or four days after the implantation of Ara-Ade, hemodynamic measurement will be examined by echocardiography with intravenous infusion of ISO or forskolin. To obtain statistical significance, at least 10 mice in each group are needed. The two doses of Ara-Ade will be tested, 20 mg/kg/day for the treating dose clinically used in virus infection and 100 mg/kg/day for a positive control. There are 3 strains tested including WT, and 12 groups in this experiment. Also, 20 mice are needed for optimization of forskolin concentration.

Implantation of Miniosmotic Pumps:

Ara-Ade will be delivered with Alzet mini-osmotic pumps (Model 2001, ALZET, CA) as previously demonstrated (Okumura et al., Circulation 2007; 116(16):1776-1783). Ara-Ade will be dissolved in 50% DMSO and 50% polyethylene glycol because Ara-Ade is poorly water-soluble. Mini-osmotic pumps will be implanted subcutaneously via a small interscapular incision in an aseptic technique.

Echocardiographic Measurement:

An Echocardiographic technique is routinely performed in our department, and will be used to measure LV contractile function (Okumura et al., PNAS 2003; 100(17):9986-9990). After measurement of body weight, mice will be anesthetized with 2.5% triburomoethanol (0.010 to 0.015 ml/g) injected intraperitoneally. Transthoracic echocardiography (Sequoia C256; Acuson, Calif.) will be performed using a 13-MHz linear ultrasound transducer. M-mode and two-dimensional echocardiographic images and M-mode tracing (sweep speed=100-200 mm/s) will be obtained. M-mode measurements of LV internal diameter (LVID) and wall thicknesses will be made from 3 consecutive beats and averaged using the leading edge-to-leading edge convention adopted by the American Society of Echocardiography. LVEF will be calculated by the cubed methods as follows: $LVEF=[(LVIDd)^3-(LVIDd)^3]/(LVIDd)^3$, where d indicates diastolic and s indicates systolic. LV percent fractional shortening (LVFS) will be calculated as $LVFS \%=[(LVIDd-LVIDs)/LVIDd] \times 100$. Heart rate will be determined from at least three consecutive RR intervals on the LV M-mode tracing.

In ISO (0.04 µg/kg per min IV for 5 minutes) or forskolin challenge, a jugular vein catheter for drug infusion will be inserted under anesthesia as described previously (Okumura et al., Circ Res. 2003; 93(4):364-371). Forskolin challenge will be performed as previously described (Iwase et al., Am J Physiol. 1996; 271(4 Pt 2):H1473-1482). Since data of intravenous infusion of forskolin in mice is not available, the concentration of forskolin (10-100 nmol/kg/min) at which maximal increase of LVEF is obtained will be first optimized. Thereafter, forskolin challenge will be performed.

Data Analysis and Statistics:

Statistical comparisons among analyses will be calculated using ANOVA with Bonferroni post hoc test. P values of <0.05 will be considered significant.

Ara-Ade (20 mg/kg/day) will be enough to inhibit LVEF in response to ISO or forskolin, because the plasma Cmax of Ara-Ade in the administration of 15 mg/kg/day is around 10 µM, which inhibits AC5 in membrane preparation of the AC5Tg hearts (FIG. 6). In addition, the degree of Ara-Ade (20 mg/kg/day)-induced decrease of LVEF is similar to that in AC5KO. Ara-Ade has no additive LVEF decrease to AC5KO in ISO- or forskolin challenge. We expect that Ara-Ade inhibits increase in LVEF of AC5Tg under basal condition, ISO- and forskolin-stimulated condition.

Example 7

Figure 7:
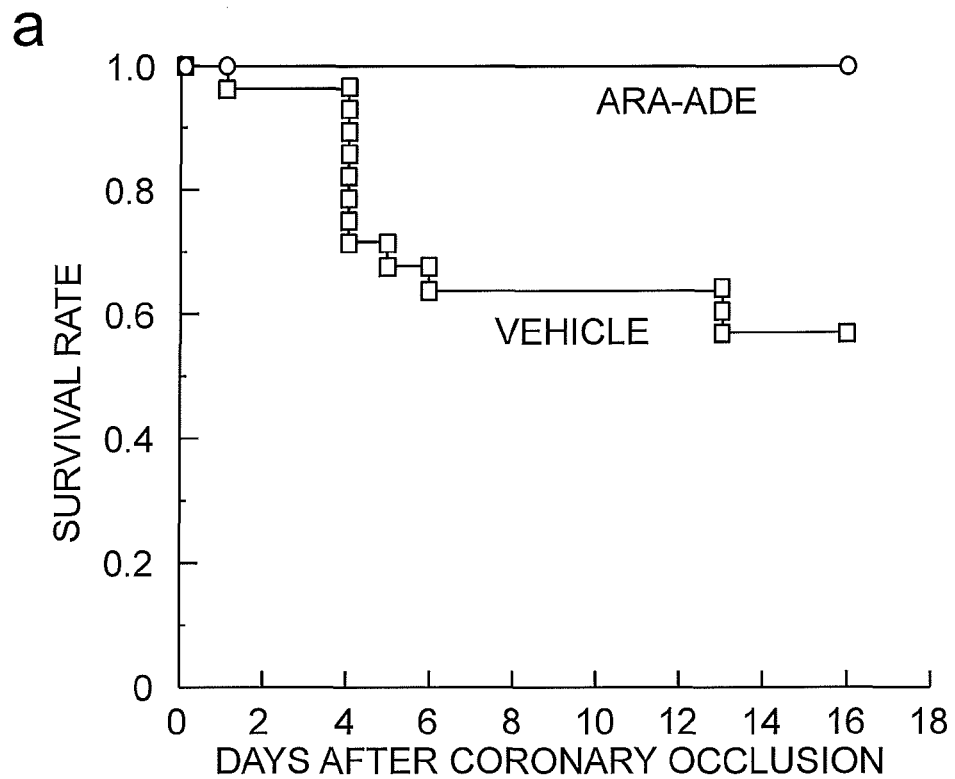
FIG. 7 demonstrates that (a) Ara-Ade increases survival rate in the post-MI period. Ara-Ade (50 mg/kg/day) was chronically infused with mini-osmotic pumps implanted subcutaneously 2-3 days before the coronary occlusion. A study of vehicle (n=25) and Ara-Ade (n=6) demonstrated significant differences in survival rate after coronary occlusion between vehicle and Ara-Ade. The chi-square test at 16 days after coronary occlusion showed significant increase in survival rate by Ara-Ade (p=0.046). However, the Log-Rank test did not reach statistical significance (p=0.08) presumably due to the small number of mice in Ara-Ade group. (b) Echocardiography was performed at 16 days after coronary occlusion. Ara-Ade prevented decrease in LVEF after MI. n=4-13.
Figure 7:
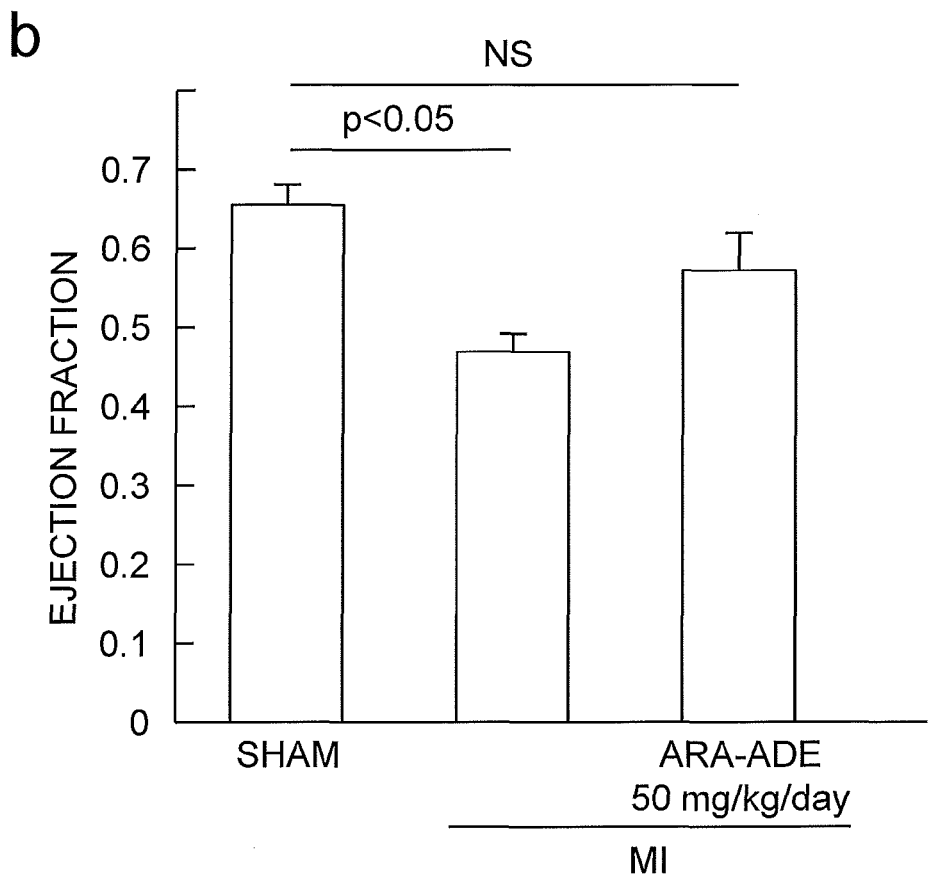

Ara-Ade Prevents the Development of LV Dysfunction, Hypertrophy and Apoptosis During the Post-MI Period Ara-Ade increases survival rate in the post-MI period (FIG. 7). We will use coronary artery occlusion to evaluate the effect of Ara-Ade in post-MI heart failure (HF). In addition to the examination of Ara-Ade, we will examine MI in AC5KO and AC5Tg to determine Ara-Ade's specificity related to AC5. Also, based on the previous report and the preliminary data, we will explore the mechanism by which Ara-Ade prevents apoptosis, focusing on the MEK1-ERK1/2 signaling pathway. Deleting AC5 activates MEK1-ERK1/2 signaling which is known to inhibit myocardial apoptosis in the heart. Also, Ara-Ade increased MEK1-ERK1/2 pathway in chronic ISO infusion model (FIG. 5), suggesting that Ara-Ade activates MEK1-ERK1/2 signaling pathway in the post-MI hearts. Therefore, we will examine the changes in MEK1-ERK1/2 signaling pathway in the post-MI hearts with chronic Ara-Ade infusion, and in AC5KO or AC5Tg. Also, we will examine survival analysis in this aim to determine whether Ara-Ade's effect on survival rate (FIG. 7) is related to prevention of post-MI HF, but no to MI itself. Accordingly, specific questions to be answered are as below.

Protocol:

LV dysfunction will be examined with echocardiography. Hypertrophy will be quantified by using the ratio of body weight/tibial length and myocyte cross sectional area. Apoptosis will be evaluated by two methods, TUNEL staining and PCR-based DNA laddering. Initiation of chronic infusion of Ara-Ade will be done 1 week after the coronary artery ligation surgery to separate the effects for post-MI HF from the protection against MI. Echocardiography measurement and the tissue harvest will be done 3 and 5 weeks after coronary artery occlusion, when LV dysfunction and histological changes are obvious (Kido et al., J Am Coll Cardiol. 2005; 46(11):2116-2124). We will use 2 doses of Ara-Ade as described in previous examples (e.g. Example 5). Also, metoprolol, an established β-blocker for post-MI HF, will be used in this model as previously demonstrated for comparison to Ara-Ade. The mortality rate during 5 weeks after the coronary occlusion in our department is roughly 30%, thus to obtain the statistical significance, at least 10 mice in each group will be used. Metoprolol will be tested only in WT, thus there are 10 groups. Accordingly, 130 mice are needed in this experiment. Experimental procedures other than left coronary occlusion, pathology and measurement of signaling molecules are described in the previous Examples.

Mouse Myocardial Infarction Model:

Permanent coronary artery occlusion is routinely performed (Yamamoto et al., J Clin Invest. 2003; 111(10):1463-1474). WT, AC5KO and AC5Tg, 4-6 month-old males (25-29 g), will be anesthetized by i.p. injection of pentobarbital sodium (60 mg/kg). A rodent ventilator will be used during the surgical procedure. The chest will be opened by a horizontal incision. Infarction will be achieved by ligating the anterior descending branch of the left coronary artery (LAD) using an 8-0 nylon suture followed by closing the chest. Sham operations will be performed with opening, suturing but not occluding, and closing the chest.

Measurements of Signaling Molecules:

Western blot analysis of changes in the survival/apoptosis signaling molecules will be performed as per previous examples. We will examine the changes including the level of protein expression and the degree of phosphorylation in MEK1-ERK1/2 signaling molecules (Raf1, MEK1 and ERK1/2). Hearts will be homogenized and subjected to SDS-PAGE and Western blot analysis. All western blot exposures will be in the linear range of detection, and the intensities of the resulting bands will be scanned and quantified by Image J software (NIH Image J website).

Pathology:

Histological analyses will be quantitatively analyzed as routinely performed. Mice will be euthanized, and body and lungs will be weighed. Also, tibial length will be measured to evaluate hypertrophy. The atria and right ventricle will be removed from the LV and septum, and the portions will be weighed. Heart sections will be stained with hematoxylin and eosin (H&E), Gomori's aldehyde fuchsin tri-chrome, and picric acid sirius red for collagen. Fibrosis area will be analyzed with NIH Image and Image J software. Terminal dUTP nick end-labeling (TUNEL) assays will be performed on LV samples as in previous examples. Photomicrographs will be obtained with a digital camera mounted on an inverted microscope. Images of 6 to 8 contiguous sections across the LV wall will be obtained at the different levels (apex, mid ventricle, and base) to measure the number of TUNEL-positive cardiac myocyte nuclei. In post-MI hearts, nuclei will be measured in the peri-infarct border and non-infarcted remote zones, where myocyte apoptosis is reported to occur after MI. For studying hypertrophy, the myocyte cross-sectional area will be measured from images captured from silver-stained 1-µm-thick methacrylate sections. Suitable cross sections will be defined as having nearly circular capillary profiles and circular-to-oval myocyte sections. No correction for oblique sectioning will be made. The outline of 100-200 myocytes will be traced in each section. METAMORPH image system software (Universal Imaging, Media, Pa.) will be used to determine myocyte cross-sectional area.

DNA Laddering:

To detect myocardial apoptosis, we will examine myocardial DNA fragmentation assay in the hearts. To visualize the DNA fragments, we will use a PCR-based technique that selectively amplifies DNA with double-stranded DNA breaks that are characteristic for apoptosis (ApoAlert LM-PCR Ladder Assay Kit; Clontech) (Engel et al., Am J Physiol Heart Circ Physiol. 2004; 287(3):H1303-1311). After a period of overnight ligation with the supplied adaptors, 50 ng of ligated genomic DNA of the heart will be amplified with 25 cycles of PCR according to the manufacturer's protocol and will be resolved on a 1.2% agarose-ethidium bromide gel. A qualitative analysis of DNA fragmentation will be performed by analyzing the pattern of low-molecular-weight DNA (180-bp multiples). Genomic DNA will be isolated from non-infarct area in LV.

Survival Rate Analysis:

Survival curves will be compared using Chi Square, Kaplan-Meier survival analysis or ANOVA with Fisher's PLSD test. Regression lines will be compared for differences in slope using the Analysis of Covariance (ANCOVA). Significance will be accepted at p<0.05.

Results:

Ara-Ade will prevent LV dysfunction and apoptosis even in the group of 20 mg/kg/day, but not hypertrophy since AC5KO did not inhibit cardiac hypertrophy. The MEK1-ERK1/2 pathway is activated by Ara-Ade administration. AC5KO will show protection against LV dysfunction and apoptosis but not hypertrophy, and activates MEK1-ERK1/2 pathway in the post-MI hearts. Ara-Ade will demonstrate no additional effect to AC5KO in terms of LV dysfunction and apoptosis. AC5Tg shows more severe LV dysfunction, apoptosis and inactivated MEK1-ERK1/2 signaling, but not hypertrophy in comparison to WT. Ara-Ade will inhibit LV dysfunction and apoptosis in AC5Tg, and in addition, Ara-Ade rescues inactivation of MEK I-ERK1/2 pathway in AC5Tg.

Example 8

Ara-Ade Prevents Death in the Post-MI Periods

Rationale:

Chronic administration of Ara-Ade, which was initiated before the coronary occlusion, increases survival rate in the post-MI period (FIG. 7). One of the major salutary effects of β-blockers is increasing survival rate in post-MI HF, indicating that such effect of β-blockers is mediated by inhibition of AC5 (Gilbert et al., Circulation. 1996; 94(11):2817-2825). Accordingly, we will examine the effect of Ara-Ade on post-MI survival. Chronic Ara-Ade infusion administration will be initiated 3 days before the coronary occlusion, survival rate will be analyzed during 5 weeks post-MI. Also, to evaluate changes in the heart, we will examine infarct size, LV function 4 weeks after the coronary occlusion. To clarify the specificity of Ara-Ade to AC5 inhibition, we will use AC5KO and AC5Tg. Previous papers demonstrated activation of MEK1-ERK1/2 pathway decreased infarct size, indicating that inhibition of AC5 reduces myocardial apoptosis and infarct size through activating MEK1-ERK1/2 signaling pathway (Darling et al., Am J Physiol Heart Circ Physiol. Oct. 1, 2005; 289(4):H1618-1626; Reid et al., Am J Physiol Heart Circ Physiol. 2005; 288(5):H2253-2259).

Protocol:

Marked differences in survival will affect the interpretation of data on LV function. Since the animals that die after MI generally have poorer LV function than those that survive, the differences between the two groups, in terms of recovery of LV function, will be blunted. It may require n=10 in each group to achieve statistical differences in recover of LV function. Accordingly, the number of mice necessary in this experiment is at least 130.

Infarct Size Determination:

Infarct size determination will be performed (Yamamoto et al., J. Clin. Invest. 2003; 111(10):1463-1474). The hearts will be removed and sliced followed by incubation with 2% triphenyltetrazolium chloride (TTC) solution. Infarct size will be determined by scanning of the slices and use of computerized morphometry software (Sigma Scan Pro 4.0, Jandel Scientific). The total volume of the infarct in each section will be calculated as the volume of a trapezium with upper and lower bases of the infarct area in each slice, multiplied by its height. The infarct size in each mouse will be defined as the sum of the volumes of all infarcts in all slices and will be expressed as a percentage of the total volume of the left ventricle.

Results:

Ara-Ade will increase survival rate in the post-MI period as demonstrated in our preliminary study. AC5KO will show increased survival rate. AC5Tg shows reduced survival rate. Ara-Ade has no additional effect to AC5KO on survival rate. Ara-Ade inhibits reduced survival rate in AC5Tg. If infarct size is similar between vehicle and Ara-Ade/AC5KO/AC5Tg, the salutary role of Ara-Ade on survival rate is related to prevention of development of post-MI HF but not to MI. If infarct size is reduced in Ara-Ade/AC5KO but increased AC5Tg, Ara-Ade inhibits MI. The potential mechanism by which Ara-Ade inhibits MI is activating MEK1-ERK1/2 signaling pathway.

Example 9

Ara-Ade Administration Reduces AC Activity

Rationale:

To confirm that the salutary effect of Ara-Ade is caused by inhibition of AC5, we will examine the changes in AC activity in post-MI HF in WT, AC5KO and AC5Tg. We will measure the cAMP content in the heart under basal, and in addition, ISO-stimulated condition to augment the decrease of cAMP by Ara-Ade.

Protocol:

cAMP content will be measured at 2 weeks after implantation of osmotic pumps (3 weeks after coronary artery occlusion. ISO-stimulation will be performed as described in previous examples, and the hearts will be removed after 5 minutes infusion of ISO (0.04 mg/kg per min IV for 5 minutes). The doses of Ara-Ade will be 20 and 100 mg/kg/day. At least 10 mice will be needed in each coronary occlusion group and the perioperative mortality in our department is 30%. Also, there are 3 strains to be tested, thus there are 12 groups and 152 mice needed in experiment.

cAMP Level in the Hearts.

cAMP content in the heart will be performed as previously described (Sato et al., Am J Physiol Heart Circ Physiol. 1999; 276(5):H1699-1705). Mice with or without chronic Ara-Ade infusion will be anesthetized, and a catheter will be inserted from the jugular vein. After infusion of normal saline or ISO (0.04 mg/kg/min) for 5 minutes, the hearts will be removed immediately (15 s) followed by freezing with liquid nitrogen. LV cAMP levels in a non-MI area will be measured by cAMP $^{125}$I-RIA kit (GE healthcare, MA). After thawing on ice-cold PBS, LV tissues will be homogenized in 1 ml of cold 6% TCA with a Polytron homogenizer. $^3$H-cAMP [4,000 counts/min (cpm)] will be added as a tracer to determine recovery. The homogenate will be centrifuged at 2500 g at 4° C. for 15 min and the TCA will be removed by extraction with water-saturated ether. The aqueous phase will be lyophilized followed by resuspension in the RIA kit buffer, and the amount of $^{125}$I-cAMP will be then counted in a gamma counter. The results will be corrected by protein concentration of each sample.

Results:

AC5KO will show decreased cAMP content in the post-MI hearts, and the degree of the decrease will be around 20% because AC5 provides 20% of total AC activity. Ara-Ade, even at 20 mg/kg/day, will decrease cAMP level in the post MI hearts, and the degree of the decrease will be similar to that of AC5KO because the plasma concentration of Ara-Ade in the administration of 20 mg/kg/day is around 10 μM, which shows a 20% decrease in cAMP accumulation in cultured cardiac myocytes. AC5Tg increases cAMP level in the post-MI hearts, and the increase is abolished by chronic Ara-Ade infusion.

Example 10

The Effects of Ara-Ade are Mediated by MEK1-ERK1/2 Signaling in Post-MI HF

Rationale:

The MEK1-ERK1/2 signaling pathway plays a major role in preventing myocardial apoptosis. AC5KO showed activated MEK1-ERK1/2 signaling, and preliminary data showed that Ara-Ade activates MEK1-ERK1/2 signaling in chronic ISO infusion model indicating that Ara-Ade prevents myocardial apoptosis through MEK1-ERK1/2 signaling pathway. To further examine and confirm the effect of Ara-Ade on MEK1-ERK1/2 pathway, we will test Ara-Ade in MEK1Tg. This model is known to protect against myocardial apoptosis, accordingly, if Ara-Ade protects against apoptosis through the MEK1-ERK1/2 pathway, when Ara-Ade is administered MEK1Tg, Ara-Ade has no additional effect in terms of apoptosis and LV dysfunction.

Protocols:

MEK1Tg has been characterized. The doses of Ara-Ade are 20 and 100 mg/kg/day, and echocardiography and tissue harvest will be examined in 3 and 5 weeks after Sham operations will be performed with opening suturing (but not occluding) and closing the chest.

Osmotic Pump Implantation.

Drugs will be delivered via Alzet mini-osmotic pumps (Model 2004, ALZET Osmotic Pumps, Cupertino, Calif.). We will optimize the maximum dose at which metoprolol does not affect basal LVEF. We will use this dose for further HF experiments. Metoprolol and Ara-Ade will be dissolved in 50% DMSO and 50% polyethylene glycol because Ara-Ade is poorly water-soluble. Vehicle is 50% DMSO and 50% polyethylene glycol alone. Mini-osmotic pumps are implanted subcutaneously via a small interscapular incision at the same time of aortic banding operation or 1 week after the coronary artery ligation.

Echocardiographic Measurement:

An echocardiographic technique is routinely performed and will be used to measure LV function. After measurement of body weight, mice will be anesthetized. Transthoracic echocardiography (Sequoia C256; Acuson, Mountain View, Calif.) will be performed using a 13-MHz linear ultrasound transducer. M-mode and two-dimensional echocardiographic images and M-mode tracing (sweep speed=100-200 mm/s) will be obtained. M-mode measurements of LV internal diameter (LVID) and wall thicknesses will be made from 3 consecutive beats and averaged using the leading edge-to-leading edge convention adopted by the American Society of Echocardiography. LVEF will be calculated by the cubed methods as follows: LVEF=[(LVIDd)$^3$(LVIDs)$^3$]/(LVIDd)$^3$, where d indicates diastolic and s indicates systolic. LV percent fractional shortening (LVFS) will be calculated as LVFS %=[(LVIDd-LVIDs)/LVIDd]×100. Heart rate will be determined from at least three consecutive RR intervals on the LV M-mode tracing.

Histological Studies:

Histological analyses will be quantitatively analyzed.

The atria and right ventricle will be removed from the LV and septum, and the portions will be weighed. Heart sections will be stained with hematoxylin and eosin (H&E), Gomori's aldehyde fuchsin tri-chrome and picric acid sirius red for collagen. Fibrosis area will be analyzed with NIH Image and Image J software (NIH).

Terminal dUTP nick end-labeling (TUNEL) assays will be performed on LV samples. The slices will be fixed in 3.7% formaldehyde solution for 24 hours, paraffin embedded, sectioned (5 μm), and mounted on glass slides.

Photomicrographs will be obtained with a digital camera. Images of 6 to 8 contiguous sections across the LV wall will be obtained at the different levels (apex, mid ventricle, and base) to measure the number of TUNEL-positive cardiac myocyte nuclei. In MI hearts, nuclei will be measured in the peri-infarct border and non-infarcted remote zones, where myocyte apoptosis is reported to occur after MI.

Data Analysis and Statistics:

All experiments will be performed using at least 15 hearts and statistical comparisons among analyses will be calculated using ANOVA with Bonferroni post hoc test. P values of <0.05 will be considered significant. Survival curves will be compared using Chi Square, Kaplan-Meier survival analysis or ANOVA with Fisher's PLSD test. Regression lines were compared for differences in slope using the Analysis of Covariance (ANCOVA). P values of <0.05 will be considered significant.

Ara-Ade will inhibit LV dysfunction, myocardial apoptosis and fibrosis in post-MI HF.

Example 12

Examine the Anti-Arrhythmic Effect of Ara-Ade Compared to a β-Blocker

Background.

In numerous clinical studies it has been demonstrated that an anti-arrhythmic effect of β-blockers contributes to preventing sudden cardiac death in HF patients. In a Beta-Blocker Heart Attack Trial (BHAT), propranolol significantly decreased sudden cardiac death by 28% in patients with a history of MI, and by 47% with a history of HF. Recently, the MERIT-HF study demonstrated that there were fewer sudden deaths in the metoprolol CR/XL group than in the placebo group. Since β-AR stimulation is known to cause arrhythmia, decreased sudden death is attributable to preventing arrhythmia occurrence. In contrast, although AC is a major downstream enzyme of β-AR, little is known about the relationship between specific AC isoforms and arrhythmogenesis. It is likely that AC5 plays a role in arrhythmogenesis. Accordingly, using isolated, perfused rat hearts, we will further examine the anti-arrhythmic effect of Ara-Ade and compare it with that of a β-blocker. Such a system is an established model to investigate anti-arrhythmic effect of drugs.

Materials and Methods.

We will use Langendorff isolated perfused rat hearts, in which various arrhythmias have been clearly demonstrated. To induce arrhythmia, a combination of low flow perfusion and norepinephrine (NE) stimulation will be performed. In this model propranolol effectively reduced arrhythmia. Thus, we will compare the anti-arrhythmic effect between Ara-Ade and propranolol. At least 15 hearts will be used in each group to obtain statistical significant data.

Langendorff Isolated Perfused Rat Heart Preparation:

The preparation will be performed as described previously. In brief, male Sprague-Dawley rats weighing 190-210 g will be killed by decapitation with a guillotine. Hearts will be removed immediately and perfused retrogradely with a Krebs-Ringer solution containing (in mM): $115NaCl$, $5KCl$, $1.2MgSO_4$, $1.2 KH_2PO_4$, $1.25CaCl_2$, $25NaHCO_3$ and 11 glucose with 1% dialyzed bovine serum albumin. The solution will be aerated with 95% $O_2$ and 5% $CO_2$, pH 7.4, under a pressure of 55-70 mmHg and a constant flow rate of 13 ml/min. The temperature of the heart will be maintained at 36° C. The first 10 min of perfusion will allow the heart to stabilize, and any heart exhibiting arrhythmia during this period will be discarded. The heart will be initially perfused at a rate of 13 ml/min for 10 min, which will be followed by a low-flow perfusion at a rate of 0.5 ml/min for 40 min. After low-flow perfusion the perfusing flow will be restored to the control level for 10 min. Although there will be occasional arrhythmias during the low-flow period, arrhythmias will be much more frequent when the flow is restored as observed. Arrhythmia will be determined in the 10-min period after the flow had been restored. Drugs will be perfused continuously into the heart by separate cannulae with a micro-infusion pump leading directly into the aorta. Ara-Ade and propranolol will be administered from the start to the end of experiment except norepinephrine (NE), which will be given from 1 min before the low-perfusion period to the end of the experiment. Propranolol and NE will be given at 1 μM. Based on $IC_{50}$ for AC5 and plasma concentration in human data, Ara-Ade will be given at 5 μM.

Measurement of ECG and the Arrhythmia Scoring System.

Electrocardiograms (ECGs) will be continuously monitored with a standard lead II throughout the experiment. A positive electrode will be attached to the apex of the heart and a negative electrode to the aorta. A typical ECG trace consists of a P-wave and a QRS complex, which occurs at regular intervals. Both atrial arrhythmias, including premature atrial contraction (PAC), and ventricular arrhythmias, including premature ventricular contraction (PVC), ventricular tachycardia (VT) and ventricular fibrillation (VF), will be observed within 10 min of the restoration of normal perfusion. VT and VF will be defined as a successive run of at least six PVCs of uniform and regular QRS complex, respectively. If there are three or more PVCs occurring within 1 min, it will be considered to be frequent. If less than three PVCs occur in a minute, it will be occasional. To enable a quantitative comparison, a scoring system modified from that in previous studies will be used. The principles of the scoring system employed will be: (1) ventricular arrhythmias will be more severe than atrial arrhythmias; (2) the severity of ventricular arrhythmias will be VF, VT, frequent PVC and occasional PVC in descending order; (3) the longer the duration of arrhythmia or the more frequent the incidence of arrhythmia, the greater the severity of arrhythmia. The score of a heart will be that of the most severe type of arrhythmia the heart exhibited. The details of the scoring system are as follows: 0, no arrhythmia; 1, atrial arrhythmias or occasional PVC; 2, frequent PVC; 3, VT (one or two episodes); 4, VT (more than three episodes) or VF (one or two episodes).

Data Analysis and Statistics.

All experiments will be performed using at least 15 hearts. Statistical comparisons among groups will be calculated using ANOVA with Bonferroni post hoc test. Comparisons between Ara-Ade and propranolol will be calculated using Student's t-test. P values of <0.05 will be considered significant. Ara-Ade will inhibit arrhythmia occurrence in Langendorff perfused rat hearts. The anti-arrhythmic effect of Ara-Ade will be equivalent to a β-blocker.

Example 13

Ara-Ade Reduced Infarct Size and Limited Reperfusion Injury

Mouse Ischemia and Reperfusion Model:

3-4 month old male C57BL/6 mice purchased from Jackson Laboratory were anesthetized by an injection of 2% 2,2,2-tribromomethanol (0.66 mg/g i.p.; Aldrich Chemical, St. Louis, Mo.). The mice were then orally intubated and mechanically ventilated. The heart was accessed via a thoracotomy at the fourth intercostals space and 7-0 silk suture passed under the left anterior descending coronary artery (LAD) at the point where it emerged from under the left atrial flap. Myocardial ischemia was achieved by occluding the LAD against a 22-gauge J-shaped stainless steel probe and verified by visually noting the regional akinesis and blanching of the left ventrical. The chest was closed in layers, with the long end of the probe remaining outside the chest wall, allowing the animal to be removed from the ventilator. After 30 min. of ischemia, reperfusion was initiated by carefully pulling the probe out form the ligature and then removing it from the chest cavity. Following the surgical procedure, the mouse was allowed to recover on a warmed surface, with supplemental oxygen delivered from a nose cone. I/R were verified by three lead electrocardiograms, which were obtained preoperatively, at the end of the ischemic interval and immediately after the initiation of reperfusion. Mice fully recovered from the surgical procedure were returned to standard animal housing conditions. The mice were under either 24 hrs of reperfusion followed by sacrifice and dual staining of the heart with TTC and Alcian Blue or kept for 4 weeks to study the heart failure progression. For the long term study post ischemia and reperfusion, the animals underwent echocardiography recording at 4 days, 2 weeks and 4 weeks after reperfusion. Ara-Ade was administered as an i.v. infusion at 0.06 mg/kg.

Pig Ischemia and Reperfusion Model:

Yorkshire pigs were under anesthesia and instrumented in accordance with established procedures. After 4 days of recovery, the pigs were subjected to ischemia and reperfusion also in accordance with established procedures. At 3 hours of coronary artery reperfusion, the animals were sacrificed and the infarct size was measures with TTC staining. Ara-Ade was administered as an i.v. infusion at 0.06 mg/kg.

Results:

The ability of the AC5 inhibitor Ara-Ade to reduce infarct size after 30 min Coronary Artery Occlusion (CAO) and 24 hr Coronary Artery Reperfusion (CAR) was examined. In mice, infarct size was lower when the drug was delivered at CAR (16%), than when administered either before CAO or CAR (21%) compared to vehicle (36%). Also of importance, Ara-Ade did not reduce arterial pressure and reflexly increase heart rate in mice. Ara-Ade also reduced infarct size in chronically instrumented conscious pigs when delivered after CAR.

What is claimed is:

1. A method of reducing infarct size and/or limiting, decreasing and/or inhibiting reperfusion injury in a patient suffering from an ischemic injury, said method comprising administering a pharmaceutically effective amount of at least one compound capable of inhibiting AC5 to the patient during or after reperfusion following the ischemic injury.

2. The method of claim 1 wherein the patient has suffered a myocardial infarction.

3. The method of claim 1 wherein the patient has Acute Coronary Syndrome.

4. The method of claim 1 wherein the compound is administered by intravenous infusion.

5. The method of claim 1 wherein the AC5 inhibiting compound inhibits heart failure progression following the ischemic injury and reperfusion.

6. The method of claim 1 wherein the AC5 inhibiting compound resembles adenosine in structure.

7. The method of claim 1 wherein the AC5 inhibiting compound inhibits reactive hyperemia in the patient.

8. The method of claim 1 wherein the AC5 inhibiting compound is 9β-D-arabinofuranosyladenine (Ara-Ade).

9. The method of claim 8 wherein the compound is administered in an amount less that 1 mg/kg.

10. The method of claim 8 wherein the compound is administered in an amount less than 0.1 mg/kg.

* * * * *